United States Patent
Truscott et al.

(10) Patent No.: US 10,593,425 B1
(45) Date of Patent: Mar. 17, 2020

(54) IDENTIFICATION AND VERIFICATION OF MEDICATION

(71) Applicant: Accenture Global Solutions Limited, Dublin (IE)

(72) Inventors: Andrew J. Truscott, Spring, TX (US); Ethan Bischoff, St. Paul, MN (US); Christopher Donnelly, Winnetka, IL (US); Jean M. Becker, Eden Prairie, MN (US)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 16/276,059

(22) Filed: Feb. 14, 2019

Related U.S. Application Data

(60) Provisional application No. 62/769,132, filed on Nov. 19, 2018.

(51) Int. Cl.
| | |
|---|---|
| *G06F 17/00* | (2019.01) |
| *G16H 20/13* | (2018.01) |
| *G06T 7/00* | (2017.01) |
| *G06N 20/00* | (2019.01) |
| *G16H 10/60* | (2018.01) |

(52) U.S. Cl.
CPC .............. *G16H 20/13* (2018.01); *G06N 20/00* (2019.01); *G06T 7/0002* (2013.01); *G16H 10/60* (2018.01)

(58) Field of Classification Search
CPC .. A61J 2205/40; B65B 3/003; G06F 19/3462; G06F 19/3456; G06Q 10/087
See application file for complete search history.

(56) References Cited

U.S. PATENT DOCUMENTS

| | | | |
|---|---|---|---|
| 5,597,995 A | 1/1997 | Williams et al. | |
| 7,028,723 B1 | 4/2006 | Alouani et al. | |
| 8,345,989 B1* | 1/2013 | Bresolin | G06K 9/00 382/218 |
| 2006/0041330 A1 | 2/2006 | Ansari et al. | |
| 2010/0018941 A1* | 1/2010 | Kerr | G01M 3/38 215/250 |
| 2010/0131097 A1 | 5/2010 | Young et al. | |
| 2013/0092700 A1* | 4/2013 | Braunstein | G07F 9/006 221/13 |
| 2019/0253258 A1* | 8/2019 | Thekadath | H04L 9/3247 |

* cited by examiner

*Primary Examiner* — Maroun P Kanaan
(74) *Attorney, Agent, or Firm* — Harrity & Harrity, LLP

(57) ABSTRACT

A device obtains prescription information relating to a medication in a container. The device causes a camera device of the device to obtain image data relating to the medication and a weighing device of the device to obtain weight data relating the medication. The device sends the prescription information, the image data, and the weight data to a different device to cause the different device to verify the medication using a machine learning model. The device receives information concerning the medication and automatically generates, based on the information concerning the medication, a message concerning the medication, wherein the message includes instructions on how much of the medication a user of the device is to take. The device causes the device or an additional device to present the message.

20 Claims, 13 Drawing Sheets

10,593,425 B1

IDENTIFICATION AND VERIFICATION OF MEDICATION

RELATED APPLICATION(S)

This application claims priority under 35 U.S.C. § 119 to U.S. Provisional Patent Application No. 62/769,132, filed on Nov. 19, 2018, the content of which is incorporated by reference herein in its entirety.

BACKGROUND

A common form of medication includes pills, capsules, tablets, and/or the like. The medication may be contained in a container. In some cases, a pharmacist, a medication filling device, and/or a pharmacist aided by a medication filling device, and/or the like may fill the container with the medication according to a prescription.

SUMMARY

According to some implementations, a device may comprise one or more memories, and one or more processors, communicatively coupled to the one or more memories, to obtain prescription information relating to a medication in a container. The one or more processors may cause, after obtaining the prescription information, a camera device of the device to obtain image data relating to the medication while the medication is in the container and may cause, after obtaining the prescription information, a weighing device of the device to obtain weight data concerning the medication while the medication is in the container. The one or more processors may send the image data and the weight data to a different device to cause the different device to identify the medication using a first machine learning model and may receive, after sending the image data and the weight data, information concerning the medication from the different device. The one or more processors may verify the medication based on the prescription information and the information concerning the medication and may cause, based on verifying the medication, the camera device to obtain additional image data relating to a seal of the container. The one or more processors may send the additional image data to the different device to cause the different device to determine an integrity of the seal using a second machine learning model and may receive, after sending the additional image data, information concerning the integrity of the seal from the different device. The one or more processors may automatically generate, based on the information concerning the medication and the information concerning the integrity of the seal, a message concerning the medication and the seal, and may cause an additional device to display the message on a display of the additional device.

According to some implementations, a non-transitory computer-readable medium may store instructions that comprise one or more instructions that, when executed by one or more processors of a device, cause the one or more processors to obtain prescription information relating to a medication in a container from a device, to obtain image data related to the medication from the device, wherein the image data was captured by a camera device of the device, and to obtain weight data related to the medication from the device, wherein the weight data was captured by a weighing device of the device. The one or more instructions may cause the one or more processors to process, using a first machine learning model, the image data and the weight data to determine information concerning the medication and to verify the medication based on the prescription information and the information concerning the medication. The one or more instructions may cause the one or more processors to obtain additional image data related to a seal of the container and to process, using a second machine learning model, the additional image data to determine information concerning the seal. The one or more instructions may cause the one or more processors to automatically generate, based on the information concerning the medication and the information concerning the seal, a message concerning the medication and the seal, and to cause the message to be sent to an additional device for display on a display of the additional device.

According to some implementations, a method may include obtaining, by a device, prescription information relating to a medication in a container, wherein the prescription information includes an identifier of the medication, a dose of the medication, and an amount of the medication. The method may include causing, by the device and after obtaining the prescription information, a camera device of the device to obtain image data relating to the medication, and causing, by the device and after obtaining the prescription information, a weighing device of the device to obtain weight data relating the medication. The method may include sending, by the device, the prescription information, the image data, and the weight data to a different device to cause the different device to verify the medication using a machine learning model, and receiving, by the device and after sending the prescription information, the image, data and the weight data to the different device, information concerning the medication. The method may include automatically generating, by the device and based on the information concerning the medication, a message concerning the medication, wherein the message includes instructions on how much of the medication a user of the device is to take, and causing, by the device, a speaker of the device to present the message to the user of the device.

DETAILED DESCRIPTION

Figure 1A:
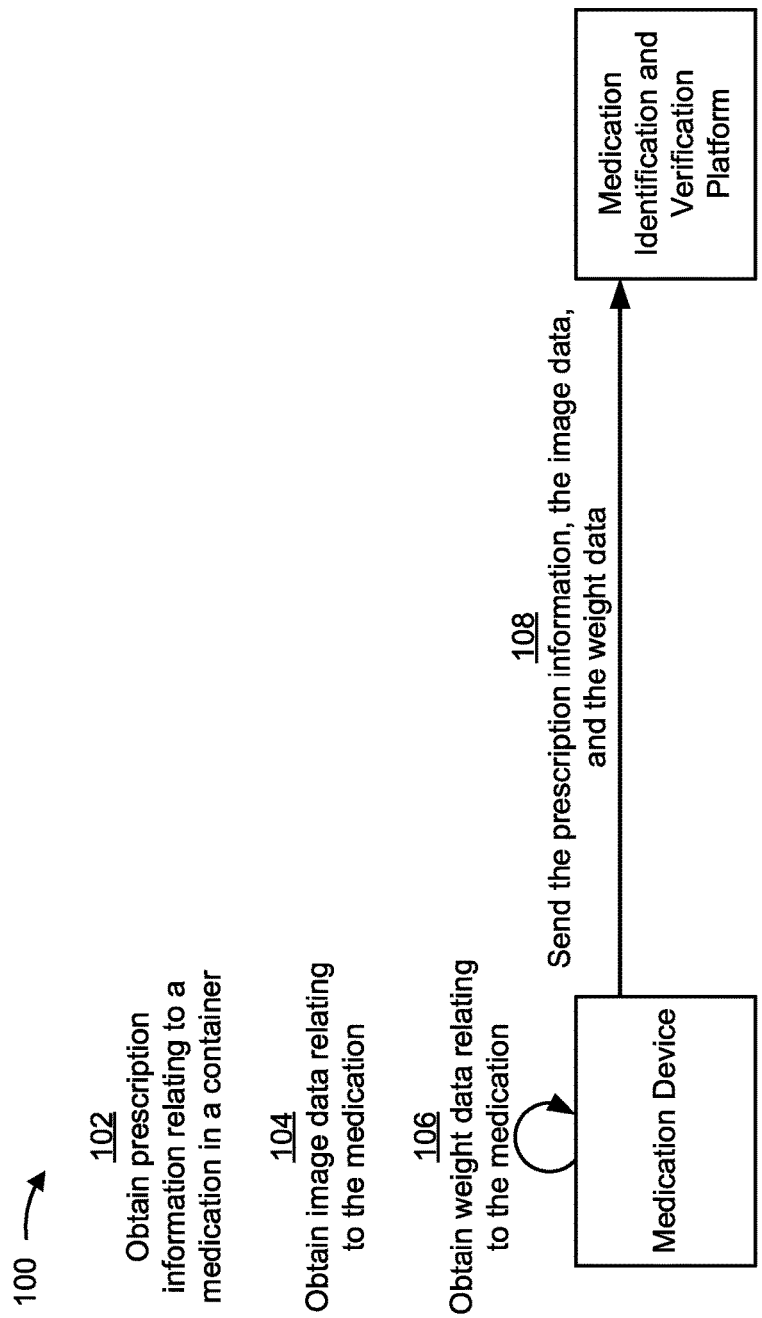
FIGS. 1A-1F are diagrams of one or more example implementations described herein.

The following detailed description of example implementations refers to the accompanying drawings. The same reference numbers in different drawings may identify the same or similar elements.

In some instances, a pharmacist, a medication filling device, and/or a pharmacist aided by a medication filling device, and/or the like may fill a container with medication (e.g., pills, capsules, tablets, and/or the like) according to one or more instructions, such as a prescription. In some cases, there is a need to identify and/or verify the medication in the container (e.g., to ensure that the prescription was filled correctly). In some cases, the medication can be removed from the container and a device can analyze the medication (e.g., perform a chemical analysis) to identify and/or verify the medication. In other cases, a different device can analyze the medication while the medication is in the container by illuminating the container with specific types of light to identify and/or verify the medication. However, these devices are sophisticated devices that require complex components to perform complicated operations, such as open a container, create chemical reactions, produce and focus specific types of light, detect characteristics of the medication, and/or the like. Additionally, the devices require extensive on-board processing resources to identify and/or verify the medication. Moreover, these devices are limited to only analyzing the medication, not the container and/or components of the container, such as a seal of the container.

According to some implementations described herein, a medication device includes at least one camera device to obtain image data relating to a medication while the medication is in a container and at least one weighing device to obtain weight data relating to the medication while the medication is in the container. In some implementations, the medication device sends prescription information relating to the medication, the image data, and the weight data to a medication identification and verification platform for the medication identification and verification platform to identify and/or verify the medication using a first machine learning model. In some implementations, the medication device receives information concerning the medication that was generated by the medication identification and verification platform and, based on the prescription information and the information concerning the medication, causes the camera device to obtain additional image data relating to a seal of the container. In some implementations, the medication device sends the additional image data to the medication identification and verification platform for the medication identification and verification platform to determine the integrity of the seal using a second machine learning model. In some implementations, the medication device receives information concerning the integrity of the seal that was generated by the medication identification and verification platform and automatically generates, based on the information concerning the medication and the information concerning the integrity of the seal, a message concerning the medication and the seal. In some implementations, the medication device causes the medication device and/or an additional device to present the message.

In this way, the medication device provides a simple device (e.g., that utilizes uncomplicated components, such as a camera device and a weighing device) for identifying and/or verifying medication. Moreover, the medication device provides similar accuracy for identifying and/or verifying medication as the complex devices discussed above. This reduces a need for elaborate components to be used to facilitate identifying and/or verifying medication. Moreover, the medication device may send data to the medication identification and verification platform for the medication identification and verification platform to analyze the data, which reduces a need for extensive processing resources to be located where the medication and/or container is being analyzed to facilitate identifying and/or verifying medication. Further, the medication device is able to facilitate determining the integrity of a seal of the container using the same, uncomplicated components that are used to facilitate identifying and/or verifying the medication.

FIGS. 1A-1F are diagrams of one or more example implementations 100 described herein. As shown in FIGS. 1A-1F, example implementation(s) 100 may include a medication device and a medication identification and verification platform. The medication device may be a communication and/or computing device and may include one or more receptacles (e.g., for holding a container), one or more camera devices (e.g., to obtain image data concerning medication in the container), one or more receptacle windows (e.g., to allow the one or more camera devices to view the medication in the container and obtain the image data), one or more weighing devices (e.g., to obtain weight data concerning medication in the container), and/or the like. The medication identification and verification platform may be a computing device, a server, a cloud computing device, and/or the like. In some implementations, the medication device and the medication identification and verification platform may be connected via a network, such as a wired network (e.g., the Internet or another data network), a wireless network (e.g., a wireless local area network, a wireless wide area network, a cellular network, etc.), and/or the like.

Some example implementations described herein concern a single medication device communicating with a single medication identification and verification platform. In some implementations, a plurality of medication devices may communicate with one or more medication identification and verification platforms. In some implementations, one or more functions of the medication identification and verification platform may be performed by a medication device instead of, or in addition to, being performed by the medication identification and verification platform. In some implementations, one or more functions of the medication device may be performed by the medication identification and verification platform instead of, or in addition to, being performed by the medication device.

In some implementations, a pharmacist, a medication filling device, a pharmacist aided by a medication filling device, and/or the like may fill a container with a medication according to a prescription. The container may be a pill container, a capsule container, a tablet container, a vial, a bottle, and/or the like. The container may be transparent or semi-transparent (e.g. to allow the medication to be seen from outside the container). The container may be filled with the medication and/or additional material, such as padding (e.g., cotton), desiccant, etc. The prescription may be a written direction for the preparation and administration of the medication by a medical practitioner. The prescription may include information that identifies the medication to be filled in the container, a dose of the medication, an amount of the medication to be filled in the container, at least one medication usage instruction, and/or the like.

In some implementations, after filling the container with the prescription, the pharmacist, the medication filling device, and/or the like may apply a closure (e.g., a lid, a cap, a cork, and/or the like), a seal (e.g., a tamper-resistant seal, a hermetic seal, a sanitary seal, a safety seal, and/or the like), and/or the like to the container. Further, the pharmacist, the medication filling device, and/or the like may apply a label to the container that includes information, such as the information included in the prescription, information concerning a pharmacy responsible for filling the prescription (e.g., a name, address, telephone number, email address, and/or the like of the pharmacy), information concerning a manufacturer of the medication (e.g., a name, address, telephone number, email address, and/or the like of the manufacture), information concerning a patient for whom the medication is prescribed (e.g., a name, address, telephone number, email address, and/or the like of the patient), an identifier (e.g., an identification string, a bar code, a quick response (QR) code, and/or the like) associated with the prescription, information concerning the medication (e.g., a description of one or more characteristics of the medication), and/or the like.

In some implementations a user of the medication device, such as the pharmacist, the patient, and/or the like may want to identify and/or verify the medication in the container and/or verify the integrity of the seal of the container. In some implementations, the user may place the container in a receptacle of the medication device to have the medication device facilitate identifying and/or verifying the medication in the container and/or verifying the integrity of the seal of the container.

As shown in FIG. 1A and by reference number 102, the medication device may obtain prescription information relating to the medication in the container. The prescription information may include the information included on the label of the container and/or the information included in the prescription. For example, the prescription information may include an identifier of the medication, information identifying a dose of the medication, information identifying an amount of the medication, and/or the like. In some implementations, the user of the medication device may cause the medication device to obtain the prescription information by interacting with the medication device. For example, the user may enter, via a user interface of the medication device, information, such as the identification string associated with the prescription, into the medication device. The medication device may perform a lookup in a data structure based on the identification string to obtain the prescription information. As another example, the user may present the label of the container to the medication device, such as position the label in a field of view of a camera device of the one or more camera devices, and the medication device may cause the camera device to obtain image data of the label. The medication device may include one or more components to facilitate positioning the label in the field of view of the camera device (e.g., an arm to rotate the container so that the label is pointed toward the camera device, a guide to position the container in front of the camera device, and/or the like). The medication device may use an image processing technique to process the image data to determine the bar code and/or the QR code of the label. The medication device may perform a lookup in a data structure based on the bar code and/or the QR code to obtain the prescription information.

As shown by reference number 104, the medication device may obtain image data relating to the medication while the medication is in the container. The image data may include image data concerning a size, a shape, a color, a pattern, a shading, a texture, a labeling, a luminance, and/or the like of at least one individual unit of the medication. In some implementations, the medication device may cause at least one camera device, of the one or more camera devices, to obtain the image data. For example, the medication device may determine that the container has been placed in a receptacle of the one or more receptacles (e.g., based on receiving weight data from a weighing device of the one or more weighing devices) and cause the at least one camera device to obtain the image data. The at least one camera device may obtain the image data via at least one receptacle window of the one or more receptacle windows (e.g., at least one receptacle window associated with the receptacle). The at least one receptacle window may allow the at least one camera device to point at a bottom of the container, at least one side of the container, a top of the container, and/or the like to obtain the image data. As another example, when causing the at least one camera device to obtain the image data, the medication device may cause the at least one camera device to determine when the container is in a field of view of the at least one camera device (e.g., the camera device may use object recognition software to recognize the container as the at least one camera device captures preview image data) and to focus on the medication in the container (e.g., adjust a focal length of the at least one camera device to focus on the medication).

In some implementations, the medication device may cause light to illuminate the container. For example, the medication device may be designed to allow ambient light to illuminate the container (e.g. via the one or more receptacle windows). As another example, the medication device may include one or more light sources (e.g., one or more light emitting diodes, one or more incandescent bulbs, one or more fluorescent lights, and/or the like) that produce the light. The light may be associated with one or more colors (e.g., "white" light, "red" light, "blue" light, "yellow" light, and/or the like). The medication device may cause the at least one camera device to obtain the image data while the container is illuminated with the light.

As shown by reference number 106, the medication device may obtain weight data relating to the medication while the medication is in the container. The weight data may include weight data concerning the container, the medication, the label of container, the closure, the seal, and/or the like. In some implementations, the medication device may cause at least one weighing device, of the one or more weighing devices, to obtain the weight data. In some implementations, the at least one weighing device may obtain weight information concerning a combined weight of the medication, the container, the label of container, the closure, the seal, and/or the like. The medication device may process the weight information (e.g., process the weight information using a tare functionality) to determine the weight data (e.g., determine a weight of just the medication).

As shown by reference number 108, the medication device may send the prescription information, the image data, and/or the weight data to the medication identification and verification platform. In some implementations, the medication identification and verification platform may obtain the prescription information, the image data, and/or the weight data from the medication device.

Figure 1B:
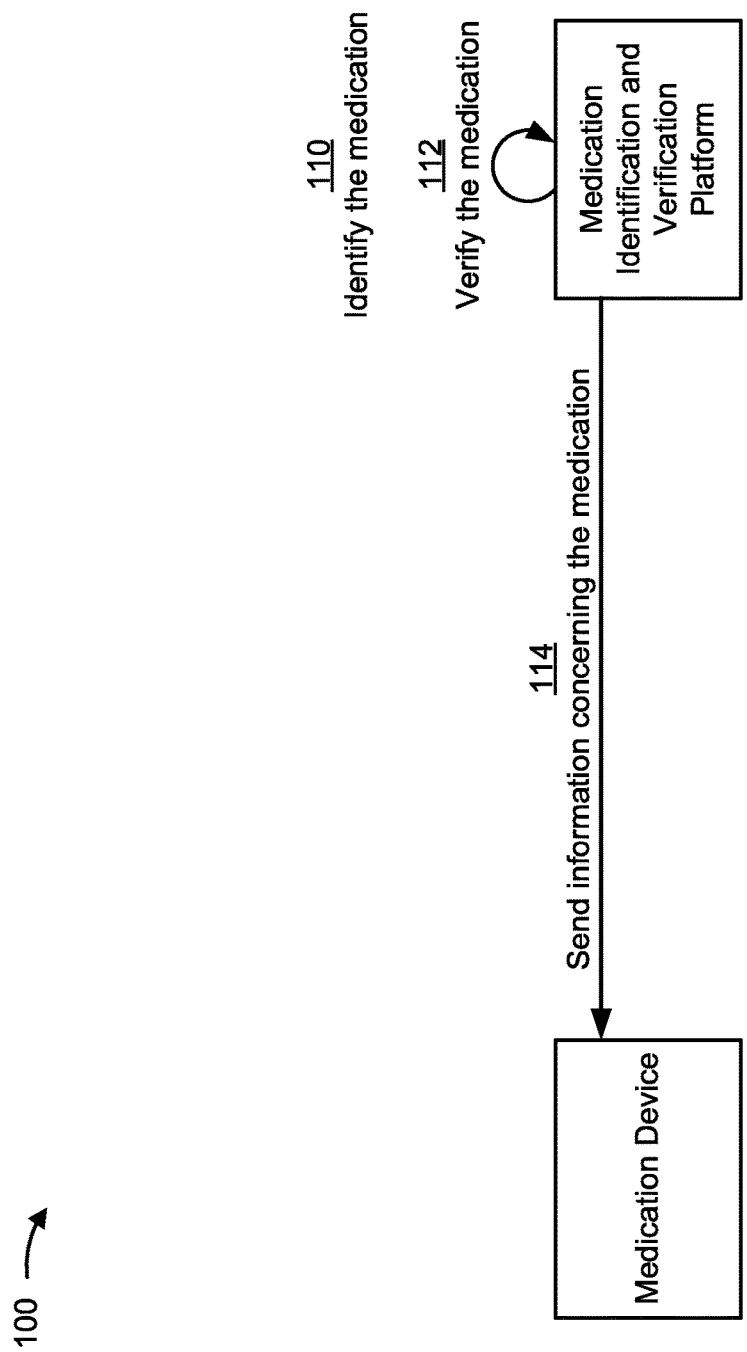

As shown in FIG. 1B and by reference number 110, the medication identification and verification platform may determine information concerning the medication to identify the medication. The medication identification and verification platform may determine the information concerning the medication based on the image data and/or the weight data. For example, the medication identification and verification platform may process the image data and/or weight data to identify the medication, a dose of the medication, an amount of the medication in the container, and/or the like.

In some implementations, the medication identification and verification platform may determine the information concerning the medication using a first machine learning model. In some implementations, the medication identification and verification platform may generate and/or train the first machine learning model. For example, the medication identification and verification platform may obtain historical information concerning medication, historical image data, and/or historical weight data (hereinafter collectively referred to as the "historical information") to generate and/or train the first machine learning model. In some implementations, the medication identification and verification platform may process the historical information to train the first machine learning model to identify a medication, a dose of medication, and an amount of medication, and/or the like, based on image data and weight data and/or to determine an identification confidence level. An identification confidence level may indicate a predicted level of accuracy concerning identification of a medication, a dose of medication, an amount of medication, and/or the like. For example, a low identification confidence level may indicate a low predicted level of accuracy (e.g., less than a particular percentage accuracy), a high identification confidence level may indicate a high predicted level of accuracy (e.g., greater than or equal to the particular percentage accuracy), and/or the like.

In some implementations, the medication identification and verification platform may perform a set of data manipulation procedures to process the historical information to generate the first machine learning model, such as a data preprocessing procedure, a model training procedure, a model verification procedure, and/or the like. For example, the medication identification and verification platform may preprocess the historical information to remove corrupt data, confidential data, irrelevant data, and/or the like. In this way, the medication identification and verification platform may organize thousands, millions, or billions of data points for machine learning and model generation.

In some implementations, the medication identification and verification platform may perform a training operation when generating the first machine learning model. For example, the medication identification and verification platform may portion the historical information into a training set (e.g., a set of data used to train the machine learning model), a validation set (e.g., a set of data used to evaluate a fit of the machine learning model and/or to fine tune the machine learning model), a test set (e.g., a set of data used to evaluate a final fit of the machine learning model), and/or the like. In some implementations, a minimum feature set may be created from pre-processing and/or dimensionality reduction of the historical information. In some implementations, the medication identification and verification platform may train the first machine learning model on this minimum feature set, thereby reducing processing required to train the first machine learning model, and may apply a classification technique to the minimum feature set.

In some implementations, the medication identification and verification platform may use a classification technique, such as a logistic regression classification technique, a random forest classification technique, a gradient boosting machine (GBM) classifier technique, and/or the like to determine a categorical outcome (e.g., that particular historical information is associated with a particular medication, a particular dose of medication, a particular amount of medication, and/or the like). Additionally, or alternatively, the medication identification and verification platform may perform a recursive feature elimination procedure to split the data of the minimum feature set into partitions and/or branches, and use the partitions and/or branches to perform predictions (e.g., that particular historical information is associated with a particular medication, a particular dose of medication, a particular amount of medication, and/or the like). Based on using the recursive feature elimination procedure, the medication identification and verification platform may reduce utilization of computing resources relative to manual, linear sorting and analysis of data points, thereby enabling use of thousands, millions, or billions of data points to train the first machine learning model, which may result in a more accurate first machine learning model than using fewer data points.

Additionally, or alternatively, the medication identification and verification platform may use a support vector machine (SVM) classifier technique to generate a non-linear boundary between data points in the training set. In this case, the non-linear boundary is used to classify test data (e.g., historical information) into a particular class (e.g., a class indicating that particular historical information is associated with a particular medication, a particular dose of medication, a particular amount of medication, and/or the like).

Additionally, or alternatively, the medication identification and verification platform may train the first machine learning model using a supervised training procedure that includes receiving input to the model from a subject matter expert, which may reduce an amount of time, an amount of processing resources, and/or the like to train the first machine learning model relative to an unsupervised training procedure. In some implementations, the medication identification and verification platform may use one or more other model training techniques, such as a neural network technique, a latent semantic indexing technique, and/or the like. For example, the medication identification and verification platform may perform an artificial neural network processing technique (e.g., using a two-layer feedforward neural network architecture, a three-layer feedforward neural network architecture, and/or the like) to perform pattern recognition with regard to patterns of particular historical information associated with a particular medication, a particular dose of medication, a particular amount of medication, and/or the like. In this case, using the artificial neural network processing technique may improve an accuracy of the first machine learning model generated by the medication identification and verification platform by being more robust to noisy, imprecise, or incomplete data, and by enabling the medication identification and verification platform to detect patterns and/or trends undetectable to human analysts or systems using less complex techniques.

In some implementations, a different device, such as a server device, may generate and train the first machine learning model. The different device may send the first machine learning model to the medication identification and verification platform. The different device may update and send (e.g., on a scheduled basis, on an on-demand basis, on a triggered basis, and/or the like) the first machine learning model to the medication identification and verification platform.

Accordingly, the medication identification and verification platform may use artificial intelligence techniques, machine learning techniques, deep learning techniques, and/or the like to determine an association between historical information and a medication, a dose of medication, an amount of medication, and/or the like.

In some implementations, the medication identification and verification platform may process, using the first machine learning model, the image data and the weight data (e.g., that were obtained from the medication device) to determine the information concerning the medication. For example, the medication identification and verification platform may process the image data and the weight data using the first machine learning model to identify the medication, a dose of the medication, and/or an amount of the medication. Further, the medication identification and verification platform, using the first machine learning model, may determine an identification confidence level relating to the identification of the medication, the dose of the medication, and the amount of the medication.

As shown by reference number 112, the medication identification and verification platform may verify the medication. In some implementations, the medication identification and verification platform may verify the medication based on the prescription information and the information concerning the medication.

For example, the medication identification and verification platform may determine that the medication has been verified if an identification of the medication, the dose, the amount of the medication, and/or the like included in the information concerning the medication corresponds (e.g., matches, matches within a threshold, and/or the like) to the prescription information. Moreover, the medication identification and verification platform may confirm the verification of the medicine if the identification confidence level satisfies a threshold (e.g., is equal to or greater than the threshold). Additionally, or alternatively, the medication identification and verification platform may determine that the medication has not been verified if the identification of the medication, the dose, the amount of the medication, and/or the like included in the information concerning the medication does not correspond (e.g., does not match, does not match within a threshold, and/or the like) to the prescription information. Moreover, the medication identification and verification platform may determine that the medication has not been verified if the identification confidence level does not satisfy a threshold (e.g., is less than the threshold).

As another example, the medication identification and verification platform may verify the medication by: determining that an identifier of the medication included in the prescription information matches an identifier of the medication included in the information concerning the medication, determining that a dose of the medication identified in the prescription information matches a dose of the medication identified in the information concerning the medication, and/or determining that an amount of the medication identified in the prescription information corresponds, within a threshold, to an amount of the medication identified in the information concerning the medication.

In some implementations, the medication identification and verification platform may include a determination of whether the medication has been verified to the information concerning the medication. In some implementations, the medication identification and verification platform, after determining whether the medication has been verified, may cause the first machine learning model to be updated. For example, the medication identification and verification platform may cause the first machine learning model to be updated (e.g., cause the first machine learning model to be retrained) based on the image data, the weight data, the prescription information, the information concerning the medication, and/or the like.

As shown by reference number 114, the medication identification and verification platform may send the information concerning the medication to the medication device. In some implementations, the medication device may obtain the information concerning the medication from the medication identification and verification platform.

Figure 1C:
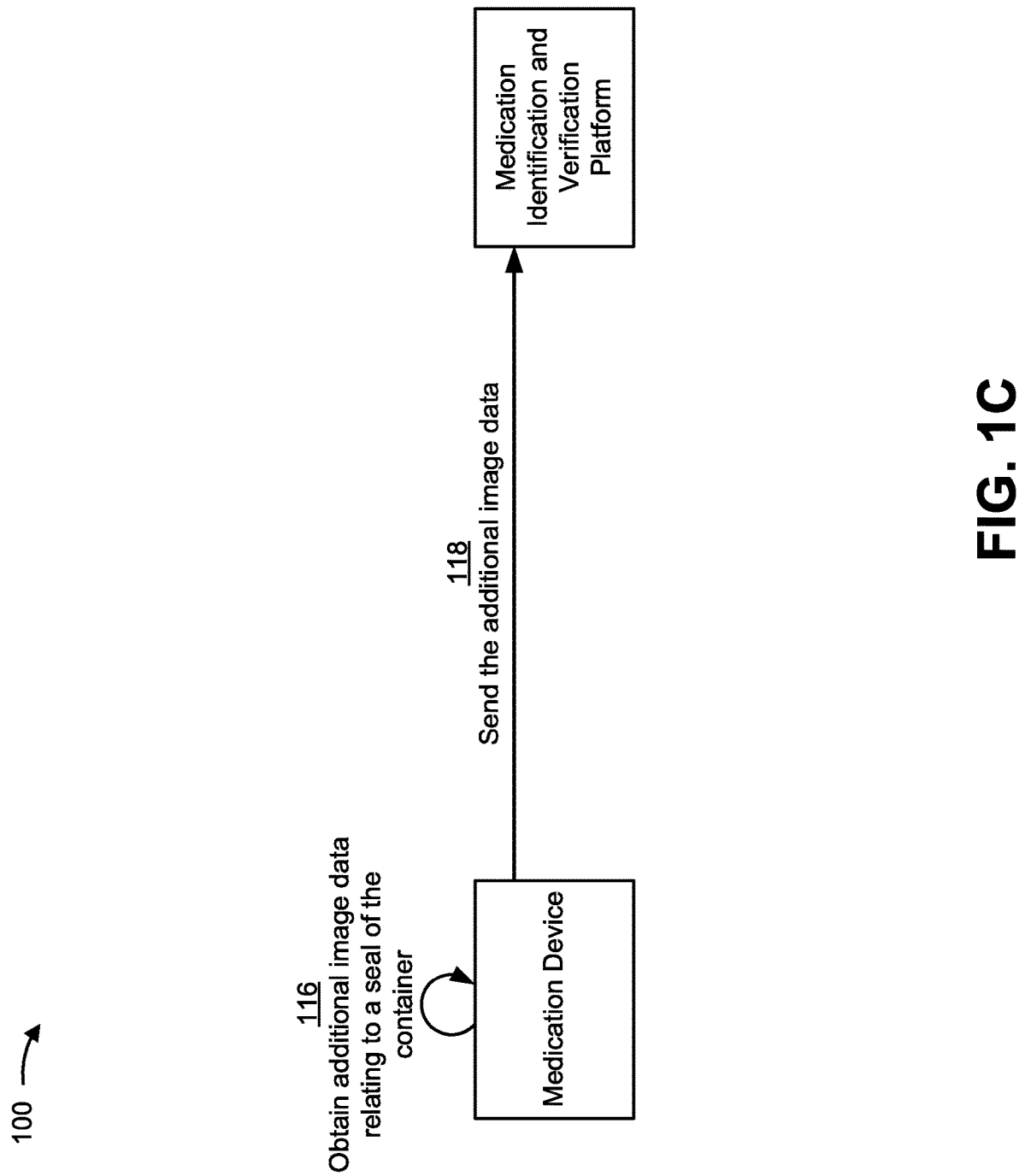

In some implementations, the medication device may process the information concerning the medication to determine that the medication has been identified and/or verified, which causes the medication device to facilitate verifying the integrity of a seal of the container. As shown in FIG. 1C and by reference number 116, the medication device may obtain additional image data relating to the seal of the container. In some implementations, the medication device may cause the at least one camera device to obtain the additional image data in a similar manner as described herein in relation to the medication device obtaining the image data (e.g., as described in relation to FIG. 1A). For example, the medication device may determine that the container has been placed in the receptacle and cause the at least one camera device to obtain the additional image data. In some implementations, the user may place the container upside-down in the receptacle to allow a particular camera device, of the one or more camera devices, to obtain the additional image data (e.g., to allow the particular camera device, which may point upwards through a receptacle window that is at the bottom of the receptacle, to point at the seal of the container when the container is placed upside-down). In some implementations, the medication device may include one or more components to facilitate positioning the seal in the field of view of the particular camera device (e.g., an arm to rotate the container so that the seal is pointed toward the camera device, a guide to position the seal in front of the camera device, and/or the like).

As shown by reference number 118, the medication device may send the additional image data to the medication identification and verification platform. In some implementations, the medication identification and verification platform may obtain the additional image data from the medication device.

Figure 1D:
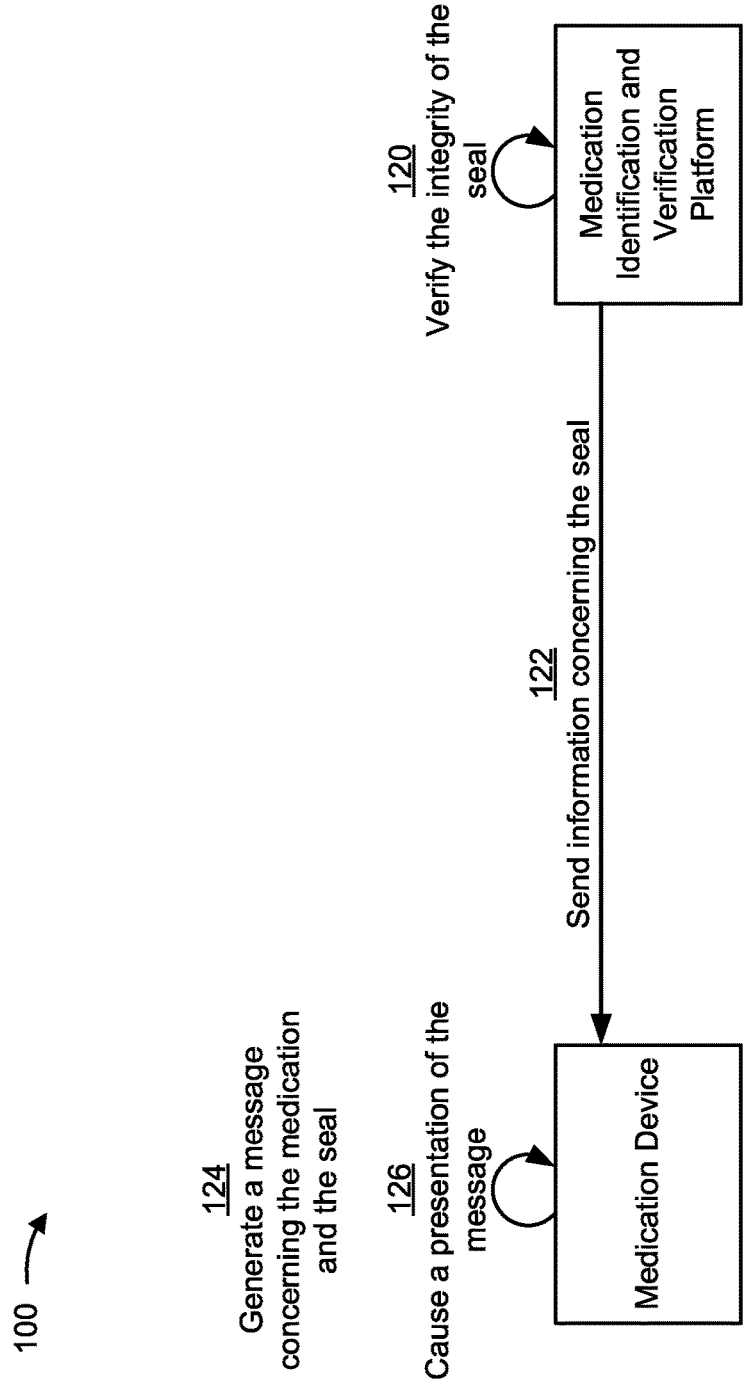

As shown in FIG. 1D and by reference number 120, the medication identification and verification platform may determine information concerning the seal to verify the integrity of the seal. The medication identification and verification platform may determine the information concerning the seal based on the additional image data. For example, the medication identification and verification platform may process the additional image data to determine the information concerning the seal, which may include information concerning the integrity of the seal (e.g., whether the seal is intact, has one or more tears, has one or more holes, shows signs of seal tampering, shows signs of seal failure, and/or the like).

In some implementations, the medication identification and verification platform may determine the information concerning the seal using a second machine learning model. In some implementations, the medication identification and verification platform may receive, generate, and/or train the second machine learning model in a similar manner as described herein in relation to the first machine learning model (e.g., as described in relation to FIG. 1B). For example, a different device, such as a server device, may generate and train the second machine learning model and send the second machine learning model to the medication identification and verification platform. As another example, the medication identification and verification platform may obtain historical additional image data and historical information concerning a seal (hereinafter collectively referred to as the "additional historical information") to generate and/or train the second machine learning model. In some implementations, the medication identification and verification platform may process the additional historical information to determine integrity issues concerning seals and/or to determine an integrity confidence level. An integrity confidence level may indicate a predicted level of accuracy concerning a determination of an integrity issue. For example, a low integrity confidence level may indicate a low predicted level of accuracy (e.g., less than a particular percentage accuracy), a high integrity confidence level may indicate a high predicted level of accuracy (e.g., greater than or equal to the particular percentage accuracy), and/or the like. In some implementations, the medication identification and verification platform may perform a set of data manipulation procedures, perform a training operation, use a classification technique, perform a recursive feature elimination procedure, and/or the like as described herein to determine an association between image data concerning a seal and an integrity issue concerning the seal.

In some implementations, the medication identification and verification platform may process, using the second machine learning model, the additional image data to determine the information concerning the seal. For example, the medication identification and verification platform may use the second machine learning model to determine, based on the additional image data, whether the seal has an integrity issue. In some implementations, the medication identification and verification platform, after determining whether the seal has an integrity issue, may cause the second machine learning model to be updated. For example, the medication identification and verification platform may cause the second machine learning model to be updated (e.g., cause the second machine learning model to be retrained) based on the additional image data, the information concerning the seal, and/or the like.

As shown by reference number 122, the medication identification and verification platform may send the information concerning the seal to the medication device. In some implementations, the medication device may obtain the information concerning the seal from the medication identification and verification platform.

As shown by reference number 124, the medication device may generate a message concerning the medication and the seal. In some implementations, the medication device may generate the message based on the information concerning the medication and the information concerning the seal. For example, the medication device may automatically generate the message upon receiving the information concerning the medication and the information concerning the seal from the medication identification and verification platform. The message may include information, such as information indicating whether the medication has been verified, whether the integrity of the seal has been verified, and/or the like; one or more instructions, such as instructions on how much of the medication a user of the medication device is to take, instructions to notify a manufacture of the medication about possible tampering of the medication and/or seal, and/or the like; one or more warnings, such as warnings that the medication may be counterfeit, warnings that the integrity of the seal has been compromised, and/or the like; and/or the like.

As shown by reference number 126, the medication device may cause a presentation of the message (e.g., cause a display to present the message, cause a speaker to present the message, and/or the like). In some implementations, the medication device may cause the presentation of the message via a display of the medication device, a speaker of the medication device, and/or the like. For example, the medication device may generate, based on the message, voice data using a text-to-speech technique and cause the speaker of the medication device to emit the voice data. In some implementations, the medication device may cause a different device to present the message (e.g., cause a display of the different device to present the message, cause a speaker of the different device to present the message, and/or the like). For example, the medication device may determine, based on the prescription information, an identifier (e.g., a telephone number, an internet protocol (IP) address, and/or the like) of the different device (e.g., a user device of the patient, a client device of the pharmacy and/or manufacture, and/or the like). The medication device may send the message, based on the identifier of the different device, to the different device. The different device, based on receiving the message, may display the message on the display of the different device and/or emit the message via the speaker of the different device.

In some implementations, a user may use the medication device to facilitate the user removing a proper dosage amount of the medication from the container. For example, a user of the medication device may remove an amount of medication from the container after viewing and/or hearing the presentation of the message and place the container in a receptacle of the medication device for the medication device to verify that the amount of medication is correct.

Figure 1E:
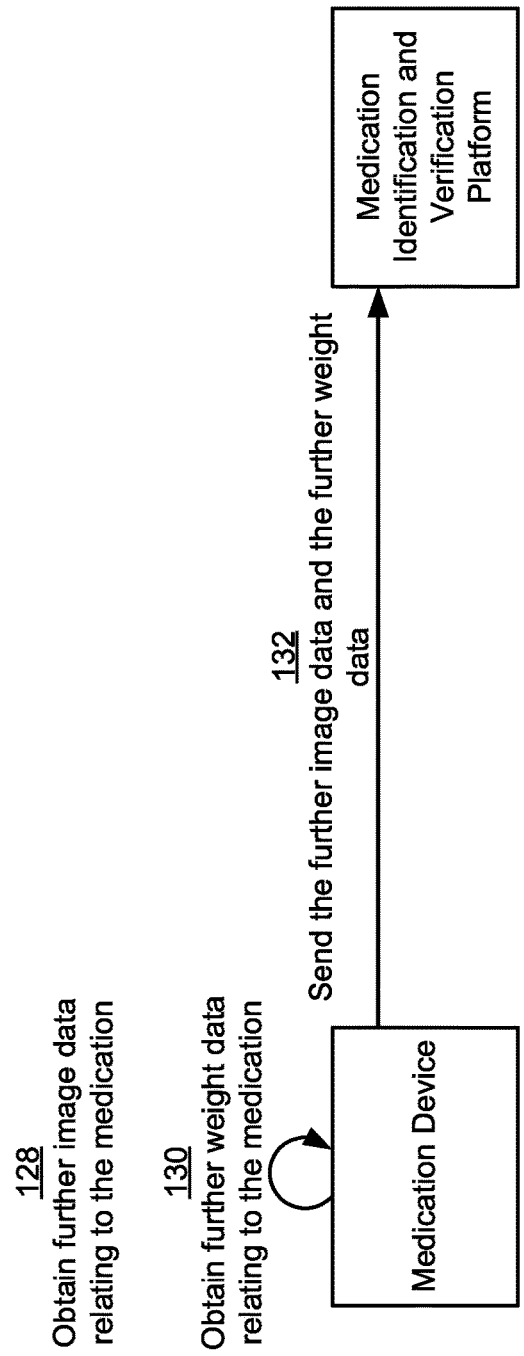

Accordingly, as shown in FIG. 1E and by reference number 128, the medication device may obtain further image data relating to the medication. For example, the medication device may cause the at least one camera device to obtain the further image data in a similar manner as described herein in relation to the medication device obtaining the image data and the additional image data (e.g., as described in relation to FIGS. 1A and 1C). For example, the medication device may determine that the container has been placed in the receptacle and cause the at least one camera device to obtain the further image data.

As shown by reference number 130, the medication device may obtain further weight data relating to the medication. In some implementations, the medication device may cause the at least one weighing device to obtain the further weight data in a similar manner as described herein in relation to the medication device obtaining the weight data (e.g., as described in relation to FIG. 1A). For example, the medication device may cause the at least one weighing device to obtain the further weight data after the user places the container in the receptacle of the medication device.

As shown by reference number 132, the medication device may send the further image data and the further weight data to the medication identification and verification platform. In some implementations, the medication identification and verification platform may obtain the further image data and the further weight data from the medication device.

Figure 1F:
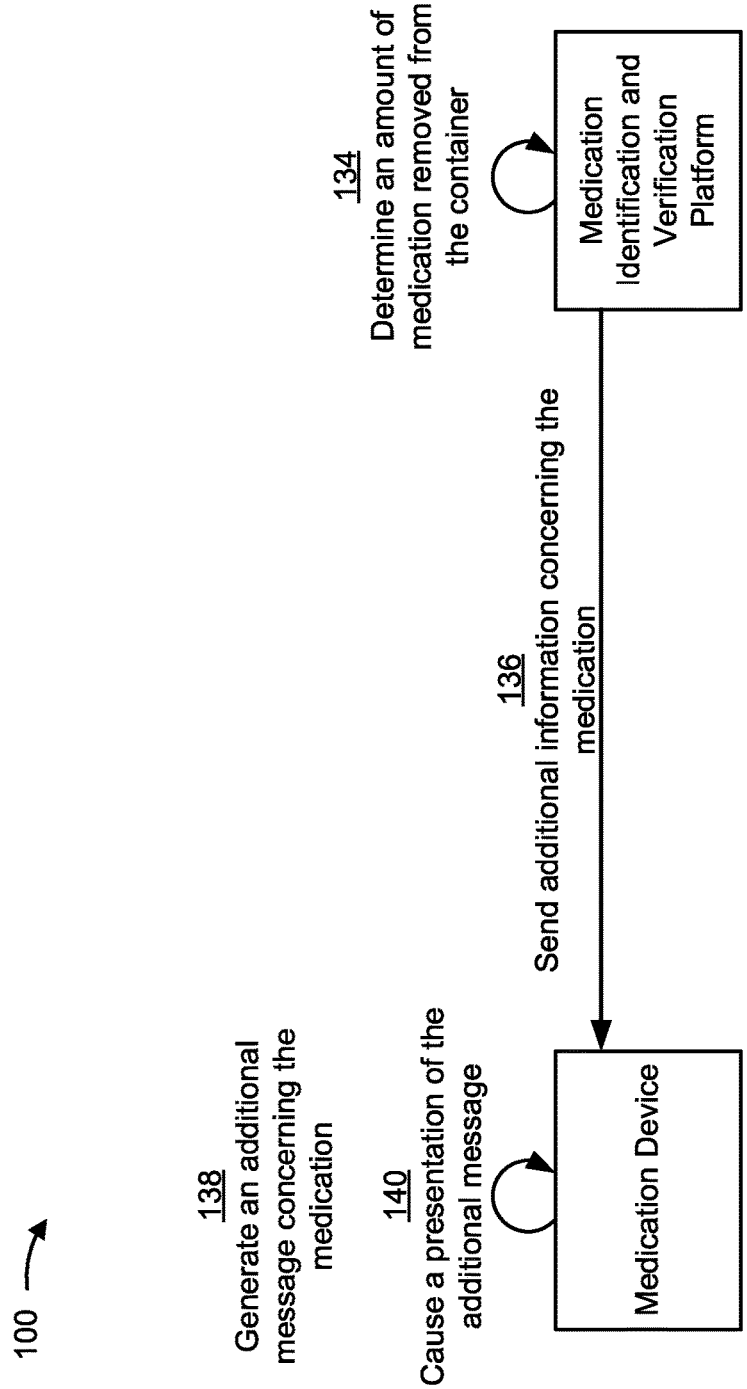

As shown in FIG. 1F and by reference number 134, the medication identification and verification platform may determine the amount of medication removed from the container. In some implementations, the medication identification and verification platform may process the further image data and the further weight data to determine additional information concerning the medication, in a similar manner as described herein in relation to the medication identification and verification platform determining the information concerning the medication (e.g., as described in relation to FIG. 1B), to facilitate determining the amount of medication removed from the container. For example, the medication identification and verification platform may process the further image data and the further weight data using the first machine learning model to identify the medication (e.g., verify that the same medication is being analyzed) and a new amount of the medication. The medication identification and verification platform may compare the new amount of the medication and the amount of the medication (e.g., an original amount of the medication before the user removed medication from the container) included in the information concerning the medication to determine the amount of medication removed from the container. The medication identification and verification platform may include information identifying the amount of medication removed from the container, information identifying the new amount of the medication, information identifying the amount of the medication, and/or the like in additional information concerning the medication.

As shown by reference number 136, the medication identification and verification platform may send the additional information concerning the medication to the medication device. In some implementations, the medication device may obtain the additional information concerning the medication from the medication identification and verification platform.

As shown by reference number 138, the medication device may generate an additional message concerning the medication. In some implementations, the medication device may generate the additional message based on the additional information concerning the medication. For example, the medication device may automatically generate the message upon receiving the additional information concerning the medication from the medication identification and verification platform. The additional message may include information, such as information on whether the amount of medication removed from the container is correct, information on how much medication is left in the container, and/or the like.

As shown by reference number 140, the medication device may cause a presentation of the additional message (e.g., cause a display to present the additional message, cause a speaker to present the additional message, and/or the like). In some implementations, the medication device may cause the medication device and/or a different device to present the additional message in a similar manner as described herein in relation to the medication device causing the presentation of the message (e.g., as described in relation to FIG. 1D).

In some implementations, information described herein may be obtained from and/or stored in a blockchain. A blockchain is a distributed database that maintains a continuously-growing list of records, called blocks, that may be linked together to form a chain. Each block in the blockchain may contain information (e.g., a timestamp, a link, etc.) relating it to a previous block and/or transaction in the blockchain. The blocks may be secured from tampering and revision. In addition, a blockchain may include a secure transaction ledger database shared by parties participating in an established, distributed network of computers. A blockchain may record a transaction (e.g., an exchange or transfer of information) that occurs in the network, thereby reducing or eliminating the need for trusted/centralized third parties. Exemplary embodiments can employ private (e.g., closed) or public (e.g., open) blockchain environments. In some cases, the parties participating in a transaction may not know the identities of any other parties participating in the transaction but may securely exchange information. Further, the distributed ledger may correspond to a record of consensus with a cryptographic audit trail that is maintained and validated by a set of independent computers.

For example, the prescription information may be stored in a blockchain and the medication device and/or medication identification and verification platform may obtain the prescription information from the blockchain. As another example, the medication device and/or the medication identification and verification platform may store the prescription information, the information concerning the medication, the information concerning the seal, the additional information concerning the medication, and/or the like in the blockchain. The blockchain may be accessible by one or more devices associated with manufacturing, filling, or distributing the medication. In this way, a record regarding the integrity of the medication, the seal, the container, and/or the like may be updated by every entity that handles the medication, the seal, the container, and/or the like.

Some example implementations described herein concern the medication identification and verification platform performing one or more functions (e.g., identifying and verifying the medication, verifying the integrity of the seal, determining the amount of medication removed from the container, and/or the like), but some implementations include the medication device performing the one or more functions. For example, in some implementations, the medication device does not communicate with the medication identification and verification platform and performs all of the one or more functions. Additionally, or alternatively, some example implementations described herein concern the medication device generating and/or causing presentation of messages, but some implementations include the medication identification and verification platform generating and/or causing the messages.

As indicated above, FIGS. 1A-1F are provided merely as an example. Other examples may differ from what is described with regard to FIGS. 1A-1F.

Figure 2A:
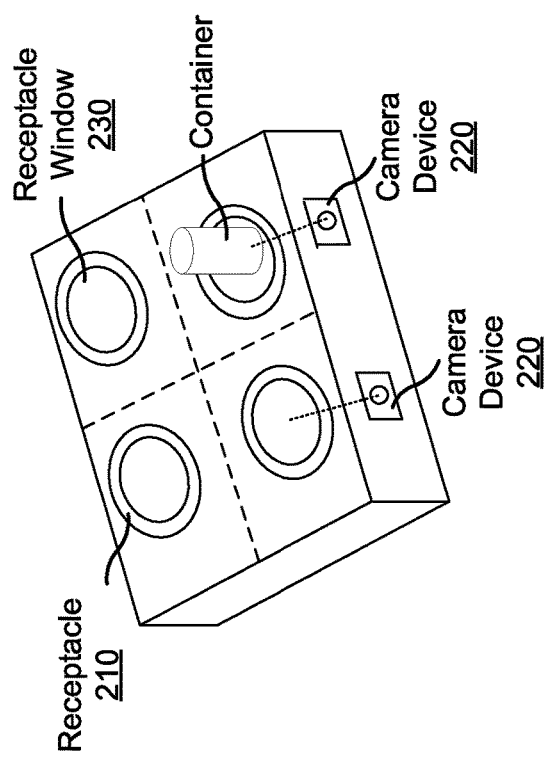
FIGS. 2A-2B are diagrams of an example medication device described herein.
Figure 2B:
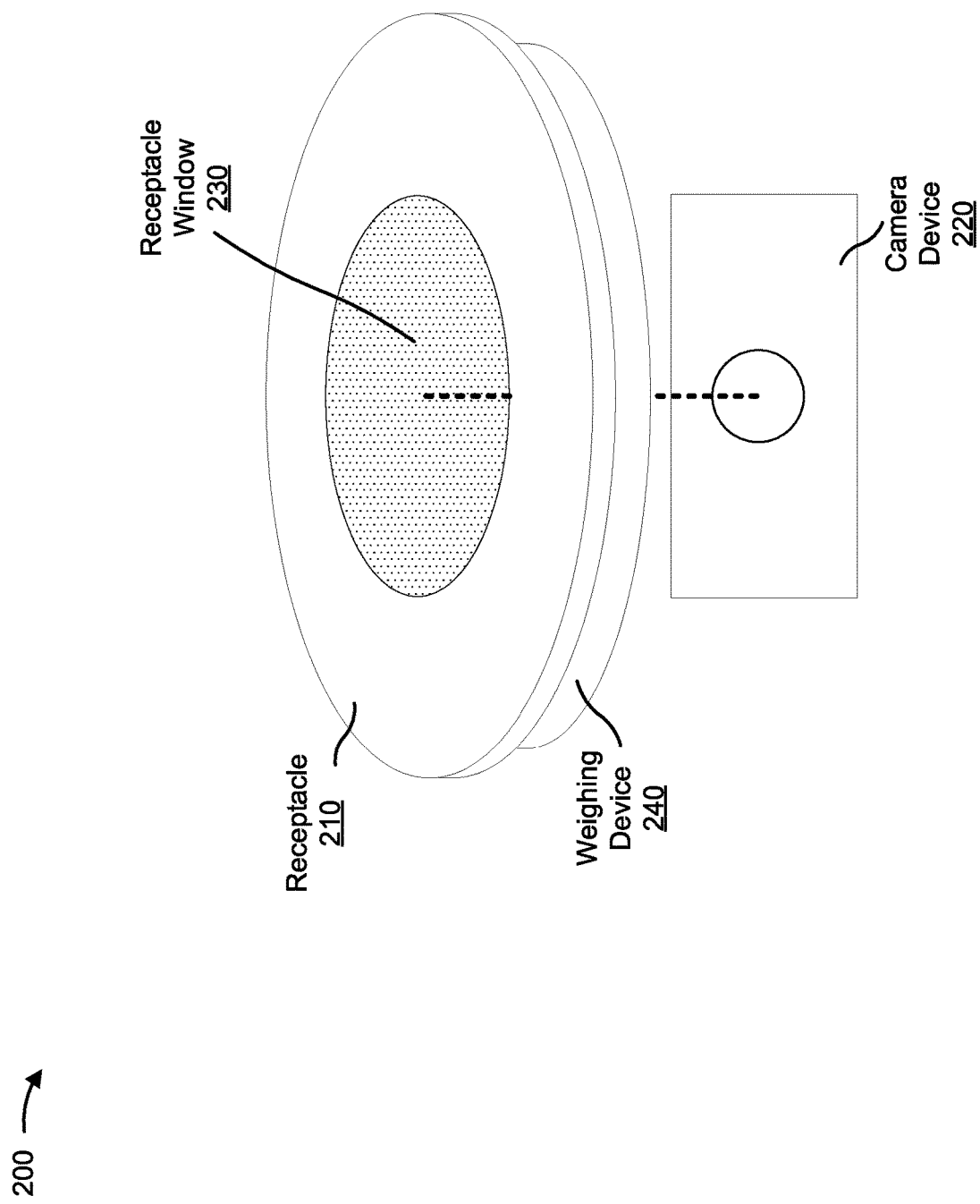

FIGS. 2A-2B are diagrams of an example medication device 200 described herein. As shown in FIG. 2A, medication device 200 may be a communication and/or computing device and may include one or more receptacles 210 (e.g., to hold one or more containers), one or more camera devices 220 (e.g., to obtain image data concerning medication in the container and/or a seal of the container), one or more receptacle windows 230 (e.g., to facilitate the one or more camera devices 220 obtaining the image data), and/or the like that perform functions, such as functions described in connection with FIGS. 1A-1F. As shown in FIG. 2B, a receptacle 210, of the one or more receptacles 210, may include a receptacle window 230, of the one or more receptacle windows 230, in and/or on the receptacle 210. A camera device 220, of the one or more camera devices 220, may be contained within the medication 200 and point at the receptacle window 230 to obtain the image data. The receptacle 210 and/or the receptacle window 230 may be attached and/or disposed on a weighing device 240, of one or more weighing devices 240 of medication device 200, that obtains weight data concerning the medication in the container.

As indicated above, FIGS. 2A-1B are provided merely as an example. Other examples may differ from what is described with regard to FIGS. 2A-2B.

Figure 3:
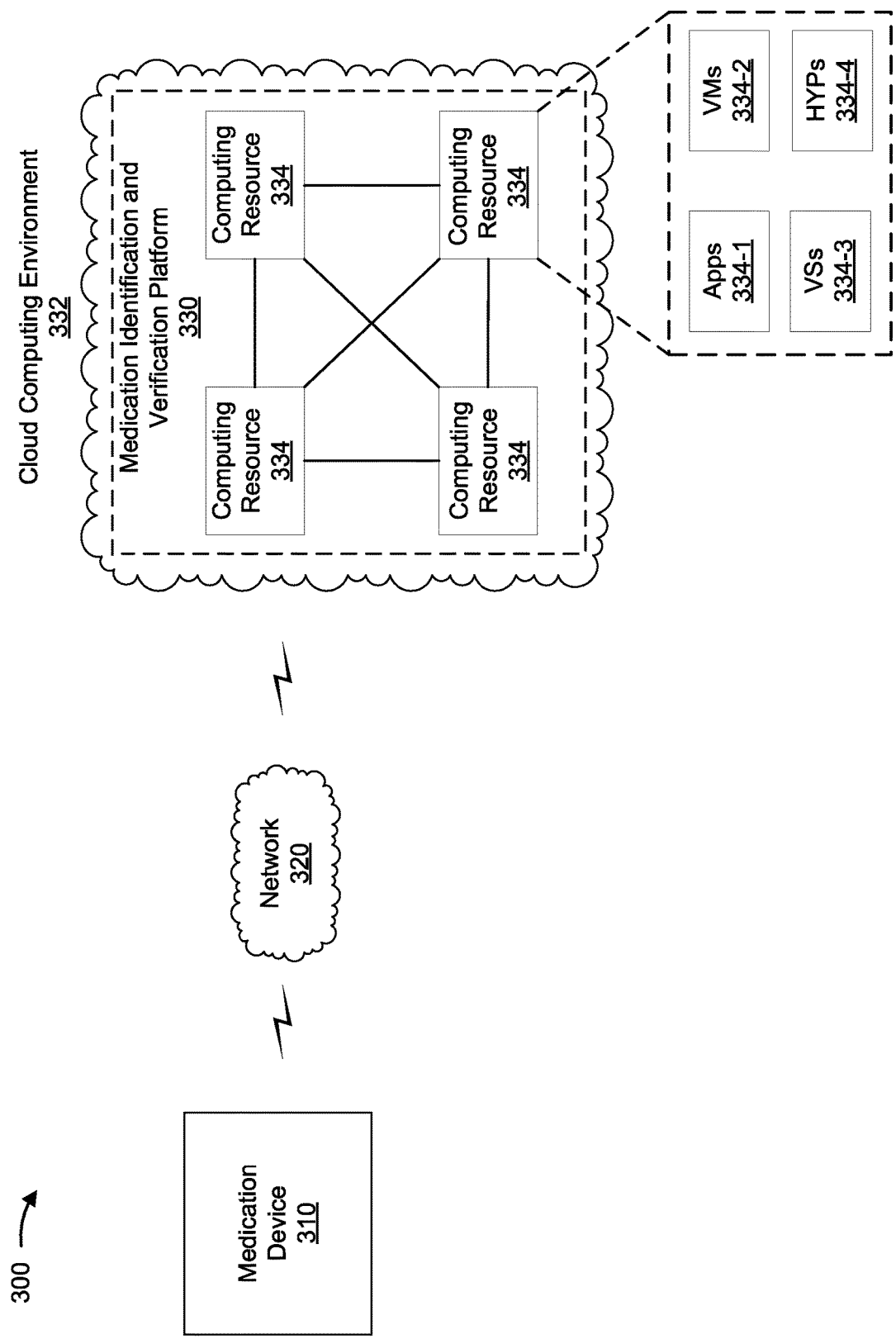
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a medication device 310, a network 320, a medication identification and verification platform 330 in a cloud computing environment 332 that includes computing resources 334, and/or the like. Devices of environment 300 may interconnect via wired connections, wireless connections, or a combination of wired and wireless connections.

Medication device 310 includes one or more devices capable of receiving, generating, storing, processing, and/or providing information, such as information described herein. For example, medication device 310 may include a computer (e.g., a desktop computer, a laptop computer, a tablet computer, a handheld computer, a server device, etc.), a mobile phone (e.g., a smart phone, a radiotelephone, etc.), an internet of things (IoT) device or smart appliance, or a similar device. In some implementations, medication device 310 may include one or more components, such as one or more receptacles to hold a container filled with medication, one or more camera devices to obtain image data relating to the medication and/or a seal of the container, one or more receptacle window to facilitate the one or more camera devices to obtain the image data, one or more weighing devices to obtain weight data relating to the medication, and/or the like. In some implementations, medication device 310 may receive information from and/or transmit information to medication identification and verification platform 330, and/or the like.

Network 320 includes one or more wired and/or wireless networks. For example, network 320 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the internet, a fiber optic-based network, a cloud computing network, a mesh network and/or the like, and/or a combination of these or other types of networks.

Medication identification and verification platform 330 includes one or more devices capable of interacting with a medication device 310 to facilitate identification and verification of medication. Medication identification and verification platform 330 may obtain, from medication device 310, prescription information relating to a medication in a container, image data related to the medication, and weight data related to the medication. Medication identification and verification platform 330 may process, using a first machine learning model, the image data and the weight data to determine information concerning the medication and verify the medication based on the prescription information and the information concerning the medication. Medication identification and verification platform 330 may obtain additional image data related to a seal of the container and may process, using a second machine learning model, the additional image data to determine information concerning the seal. Medication identification and verification platform 330 may automatically generate, based on the information concerning the medication and the information concerning the seal, a message concerning the medication and the seal and may cause the message to be sent to an additional device, such as medication device 310, for presentation by the additional device.

In some implementations, medication identification and verification platform 330 may be designed to be modular such that certain software components may be swapped in or out depending on a particular need. As such, medication identification and verification platform 330 may be easily and/or quickly reconfigured for different uses. In some implementations, medication identification and verification platform 330 may receive information from and/or transmit information to medication device 310, such as via network 320.

In some implementations, as shown, medication identification and verification platform 330 may be hosted in a cloud computing environment 332. Notably, while implementations described herein describe medication identification and verification platform 330 as being hosted in cloud computing environment 332, in some implementations, medication identification and verification platform 330 may be non-cloud-based (i.e., may be implemented outside of a cloud computing environment) or may be partially cloud-based.

Cloud computing environment 332 includes an environment that hosts medication identification and verification platform 330. Cloud computing environment 332 may provide computation, software, data access, storage, etc. services that do not require end-user knowledge of a physical location and configuration of system(s) and/or device(s) that hosts medication identification and verification platform 330. As shown, cloud computing environment 332 may include a group of computing resources 334 (referred to collectively as "computing resources 334" and individually as "computing resource 334").

Computing resource 334 includes one or more personal computers, workstation computers, server devices, or other types of computation and/or communication devices. In some implementations, computing resource 334 may host medication identification and verification platform 330. The cloud resources may include compute instances executing in computing resource 334, storage devices provided in computing resource 334, data transfer devices provided by computing resource 334, etc. In some implementations, computing resource 334 may communicate with other computing resources 334 via wired connections, wireless connections, or a combination of wired and wireless connections.

As further shown in FIG. 3, computing resource 334 includes a group of cloud resources, such as one or more applications ("APPs") 334-1, one or more virtual machines ("VMs") 334-2, virtualized storage ("VSs") 334-3, one or more hypervisors ("HYPs") 334-4, and/or the like.

Application 334-1 includes one or more software applications that may be provided to or accessed by medication device 310. Application 334-1 may eliminate a need to install and execute the software applications on medication device 310. For example, application 334-1 may include software associated with medication identification and verification platform 330 and/or any other software capable of being provided via cloud computing environment 332. In some implementations, one application 334-1 may send/receive information to/from one or more other applications 334-1, via virtual machine 334-2.

Virtual machine 334-2 includes a software implementation of a machine (e.g., a computer) that executes programs like a physical machine. Virtual machine 334-2 may be either a system virtual machine or a process virtual machine, depending upon use and degree of correspondence to any real machine by virtual machine 334-2. A system virtual machine may provide a complete system platform that supports execution of a complete operating system ("OS"). A process virtual machine may execute a single program, and may support a single process. In some implementations, virtual machine 334-2 may execute on behalf of a user (e.g., a user of medication device 310), and may manage infrastructure of cloud computing environment 332, such as data management, synchronization, or long-duration data transfers.

Virtualized storage 334-3 includes one or more storage systems and/or one or more devices that use virtualization techniques within the storage systems or devices of computing resource 334. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored.

This may enable optimization of storage use, server consolidation, and/or performance of non-disruptive file migrations.

Hypervisor 334-4 may provide hardware virtualization techniques that allow multiple operating systems (e.g., "guest operating systems") to execute concurrently on a host computer, such as computing resource 334. Hypervisor 334-4 may present a virtual operating platform to the guest operating systems, and may manage the execution of the guest operating systems. Multiple instances of a variety of operating systems may share virtualized hardware resources.

The number and arrangement of devices and networks shown in FIG. 3 are provided as one or more examples. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
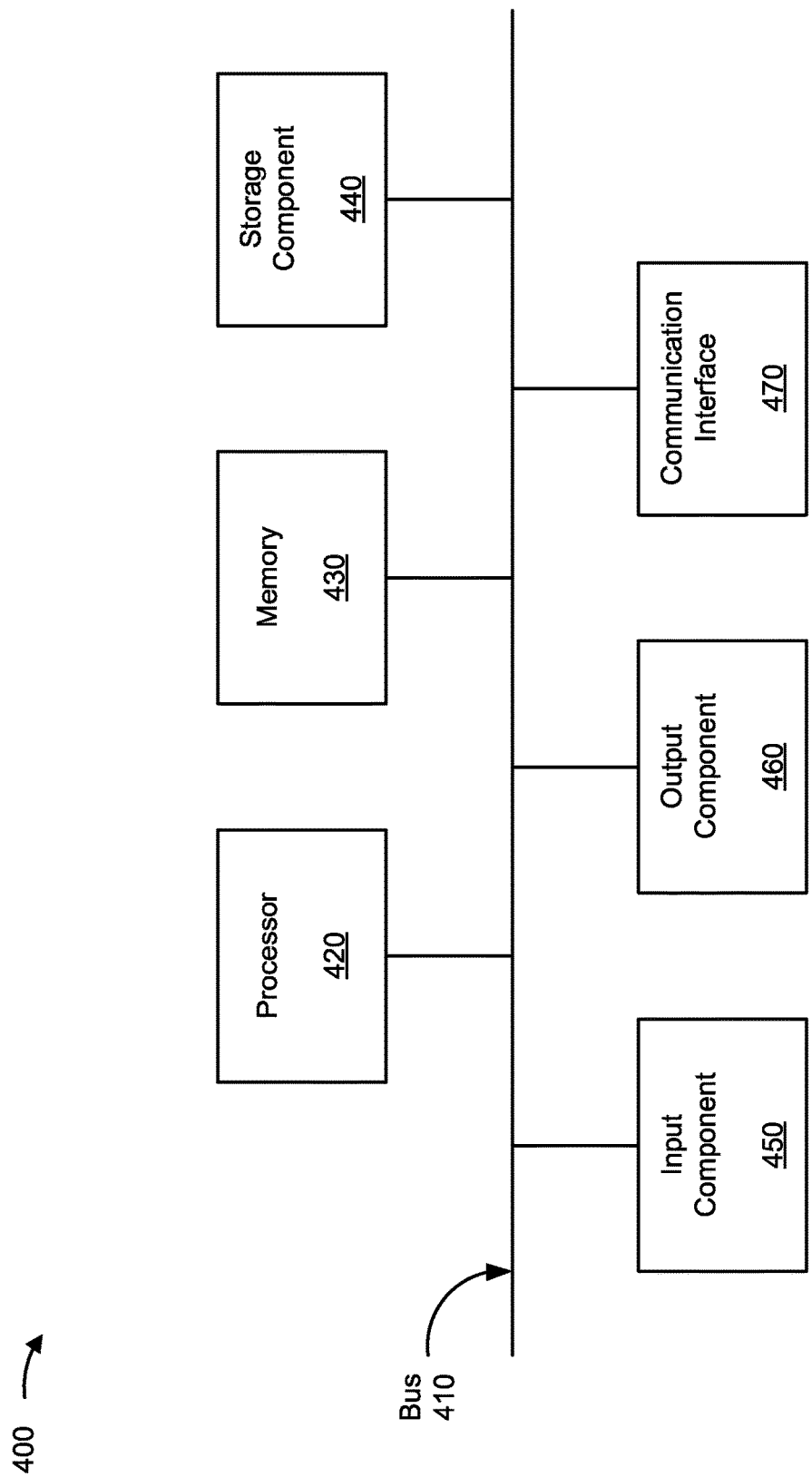
FIG. 4 is a diagram of example components of one or more devices of FIG. 2 and/or FIG. 3.

FIG. 4 is a diagram of example components of a device 400. Device 400 may correspond to medication device 310, medication identification and verification platform 330, computing resource 334, and/or the like. In some implementations, medication device 310, medication identification and verification platform 330, computing resource 334, and/or the like may include one or more devices 400 and/or one or more components of device 400. As shown in FIG. 4, device 400 may include a bus 410, a processor 420, a memory 430, a storage component 440, an input component 450, an output component 460, and/or a communication interface 470.

Bus 410 includes a component that permits communication among multiple components of device 400. Processor 420 is implemented in hardware, firmware, and/or a combination of hardware and software. Processor 420 takes the form of a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 420 includes one or more processors capable of being programmed to perform a function. Memory 430 includes a random-access memory (RAM), a read only memory (ROM), and/or another type of dynamic or static storage device (e.g., a flash memory, a magnetic memory, and/or an optical memory) that stores information and/or instructions for use by processor 420.

Storage component 440 stores information and/or software related to the operation and use of device 400. For example, storage component 440 may include a hard disk (e.g., a magnetic disk, an optical disk, and/or a magneto-optic disk), a solid-state drive (SSD), a compact disc (CD), a digital versatile disc (DVD), a floppy disk, a cartridge, a magnetic tape, and/or another type of non-transitory computer-readable medium, along with a corresponding drive.

Input component 450 includes a component that permits device 400 to receive information, such as via user input (e.g., a touch screen display, a keyboard, a keypad, a mouse, a button, a switch, and/or a microphone). Additionally, or alternatively, input component 450 may include a component for determining location (e.g., a global positioning system (GPS) component) and/or a sensor (e.g., an accelerometer, a gyroscope, an actuator, another type of positional or environmental sensor, and/or the like). Output component 460 includes a component that provides output information from device 400 (via, e.g., a display, a speaker, a haptic feedback component, an audio or visual indicator, and/or the like).

Communication interface 470 includes a transceiver-like component (e.g., a transceiver, a separate receiver, a separate transmitter, and/or the like) that enables device 400 to communicate with other devices, such as via a wired connection, a wireless connection, or a combination of wired and wireless connections. Communication interface 470 may permit device 400 to receive information from another device and/or provide information to another device. For example, communication interface 470 may include an Ethernet interface, an optical interface, a coaxial interface, an infrared interface, a radio frequency (RF) interface, a universal serial bus (USB) interface, a Wi-Fi interface, a cellular network interface, and/or the like.

Device 400 may perform one or more processes described herein. Device 400 may perform these processes based on processor 420 executing software instructions stored by a non-transitory computer-readable medium, such as memory 430 and/or storage component 440. As used herein, the term "computer-readable medium" refers to a non-transitory memory device. A memory device includes memory space within a single physical storage device or memory space spread across multiple physical storage devices.

Software instructions may be read into memory 430 and/or storage component 440 from another computer-readable medium or from another device via communication interface 470. When executed, software instructions stored in memory 430 and/or storage component 440 may cause processor 420 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 4 are provided as an example. In practice, device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

Figure 5:
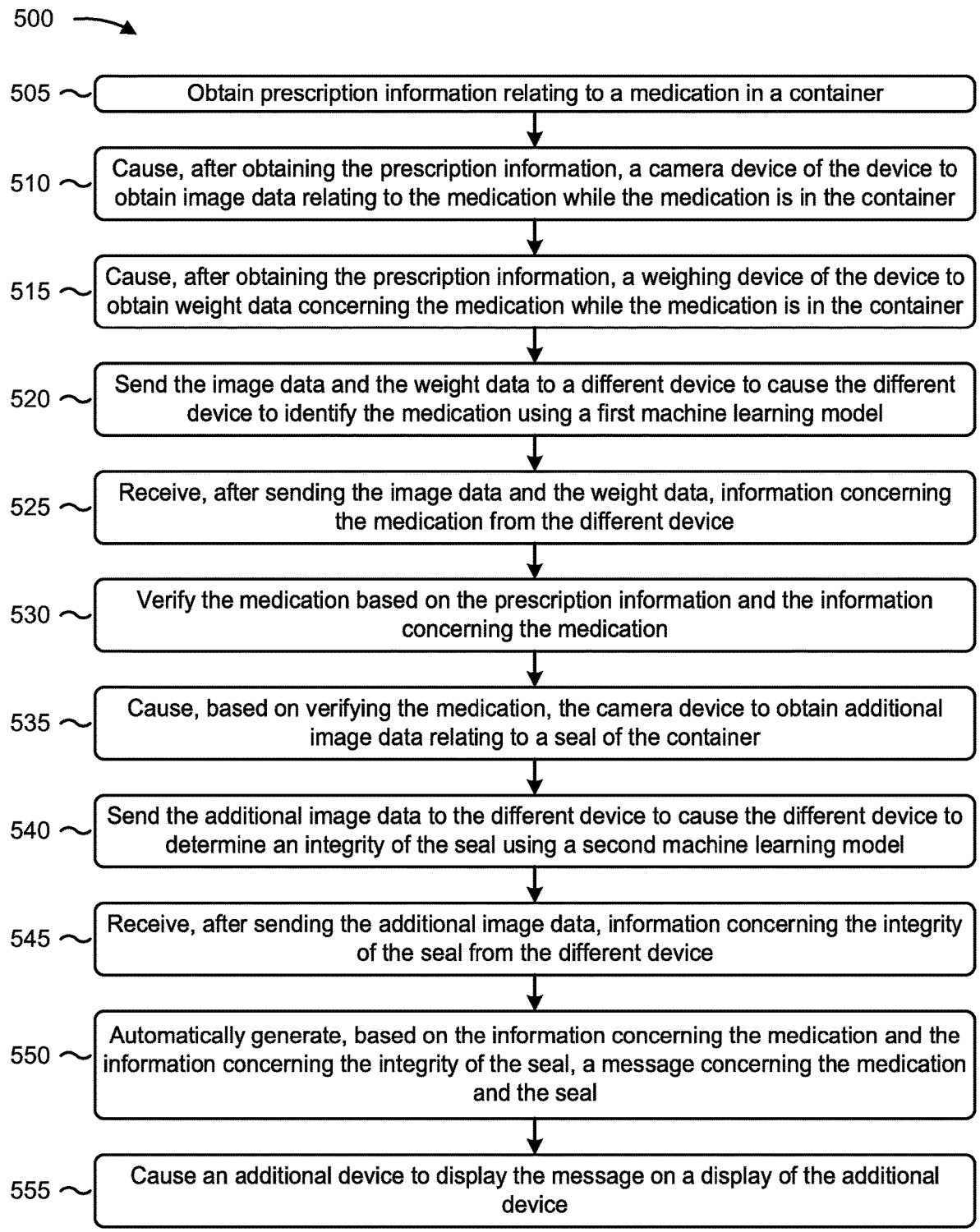
FIGS. 5-7 are flow charts of example processes for identification and verification of medication.

FIG. 5 is a flow chart of an example process 500 for identification and verification of medication. In some implementations, one or more process blocks of FIG. 5 may be performed by a medication device (e.g., medication device 310). In some implementations, one or more process blocks of FIG. 5 may be performed by another device or a group of devices separate from or including the medication device, such as a medication identification and verification platform (e.g., medication identification and verification platform 330) and/or the like.

As shown in FIG. 5, process 500 may include obtaining prescription information relating to a medication in a container (block 505). For example, the medication device (e.g., using processor 420, memory 430, storage component 440, input component 450, output component 460, communication interface 470 and/or the like) may obtain prescription information relating to a medication in a container, as described above.

As further shown in FIG. 5, process 500 may include causing, after obtaining the prescription information, a camera device of the device to obtain image data relating to the medication while the medication is in the container (block 510). For example, the medication device (e.g., using processor 420, memory 430, storage component 440, input component 450, output component 460, communication interface 470 and/or the like) may cause, after obtaining the prescription information, a camera device of the device to obtain image data relating to the medication while the medication is in the container, as described above.

As further shown in FIG. 5, process 500 may include causing, after obtaining the prescription information, a weighing device of the device to obtain weight data concerning the medication while the medication is in the container (block 515). For example, the medication device (e.g., using processor 420, memory 430, storage component 440, input component 450, output component 460, communication interface 470 and/or the like) may cause, after obtaining the prescription information, a weighing device of the device to obtain weight data concerning the medication while the medication is in the container, as described above.

As further shown in FIG. 5, process 500 may include sending the image data and the weight data to a different device to cause the different device to identify the medication using a first machine learning model (block 520). For example, the medication device (e.g., using processor 420, memory 430, storage component 440, input component 450, output component 460, communication interface 470 and/or the like) may send the image data and the weight data to a different device to cause the different device to identify the medication using a first machine learning model, as described above.

As further shown in FIG. 5, process 500 may include receiving, after sending the image data and the weight data, information concerning the medication from the different device (block 525). For example, the medication device (e.g., using processor 420, memory 430, storage component 440, input component 450, output component 460, communication interface 470 and/or the like) may receive, after sending the image data and the weight data, information concerning the medication from the different device, as described above.

As further shown in FIG. 5, process 500 may include verifying the medication based on the prescription information and the information concerning the medication (block 530). For example, the medication device (e.g., using processor 420, memory 430, storage component 440, input component 450, output component 460, communication interface 470 and/or the like) may verify the medication based on the prescription information and the information concerning the medication, as described above.

As further shown in FIG. 5, process 500 may include causing, based on verifying the medication, the camera device to obtain additional image data relating to a seal of the container (block 535). For example, the medication device (e.g., using processor 420, memory 430, storage component 440, input component 450, output component 460, communication interface 470 and/or the like) may cause, based on verifying the medication, the camera device to obtain additional image data relating to a seal of the container, as described above.

As further shown in FIG. 5, process 500 may include sending the additional image data to the different device to cause the different device to determine an integrity of the seal using a second machine learning model (block 540). For example, the medication device (e.g., using processor 420, memory 430, storage component 440, input component 450, output component 460, communication interface 470 and/or the like) may send the additional image data to the different device to cause the different device to determine an integrity of the seal using a second machine learning model, as described above.

As further shown in FIG. 5, process 500 may include receiving, after sending the additional image data, information concerning the integrity of the seal from the different device (block 545). For example, the medication device (e.g., using processor 420, memory 430, storage component 440, input component 450, output component 460, communication interface 470 and/or the like) may receive, after sending the additional image data, information concerning the integrity of the seal from the different device, as described above.

As further shown in FIG. 5, process 500 may include automatically generating, based on the information concerning the medication and the information concerning the integrity of the seal, a message concerning the medication and the seal (block 550). For example, the medication device (e.g., using processor 420, memory 430, storage component 440, input component 450, output component 460, communication interface 470 and/or the like) may automatically generate, based on the information concerning the medication and the information concerning the integrity of the seal, a message concerning the medication and the seal, as described above.

As further shown in FIG. 5, process 500 may include causing an additional device to display the message on a display of the additional device (block 555). For example, the medication device (e.g., using processor 420, memory 430, storage component 440, input component 450, output component 460, communication interface 470 and/or the like) may cause an additional device to display the message on a display of the additional device, as described above.

Process 500 may include additional implementations, such as any single implementation or any combination of implementations described below and/or in connection with one or more other processes described elsewhere herein.

In some implementations, the prescription information may include at least one of an identifier of the medication, information identifying a dose of the medication, and/or information identifying an amount of the medication. In some implementations, when obtaining the prescription information, the medication device may cause the camera device to obtain further image data relating to a label of the container, may process the further image data using an image processing technique to obtain the prescription information. In some implementations, when causing the camera device to obtain the image data relating to the medication, the medication device may cause ambient light to illuminate the container, and may cause the camera device to obtain the image data while the container is illuminated with the ambient light.

In some implementations, when verifying the medication based on the prescription information and the information concerning the medication, the medication device may determine that an identifier of the medication included in the prescription information matches an identifier of the medication included in the information concerning the medication; may determine that a dose of the medication identified in the prescription information matches a dose of the medication identified in the information concerning the medication; may determine that an amount of the medication identified in the prescription information corresponds, within a threshold, to an amount of the medication identified in the information concerning the medication; and may verify the medication based on determining that the identifier of the medication included in the prescription information matches the identifier of the medication included in the information concerning the medication, determining that the dose of the medication identified in the prescription information matches the dose of the medication identified in the information concerning the medication, and determining that the amount of the medication identified in the prescription information corresponds, within the threshold, to the amount of the medication identified in the information concerning the medication.

In some implementations, when causing the camera device to obtain the additional image data relating to the seal of the container, the medication device may determine that the container has been placed in a receptacle of the device, and may cause the camera device to obtain the additional image data via a window of the receptacle. In some implementations, when causing the additional device to display the message on the display of the additional device, the medication device may determine, based on the prescription information, an identifier of the additional device, and may send, based on the identifier of the additional device, the message to the additional device are.

In some implementations, the medication device may store the information concerning the medication and the information concerning the integrity of the seal in a blockchain. In some implementations, the blockchain is accessible by at least one device associated with manufacturing, filling, or distributing the medication.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
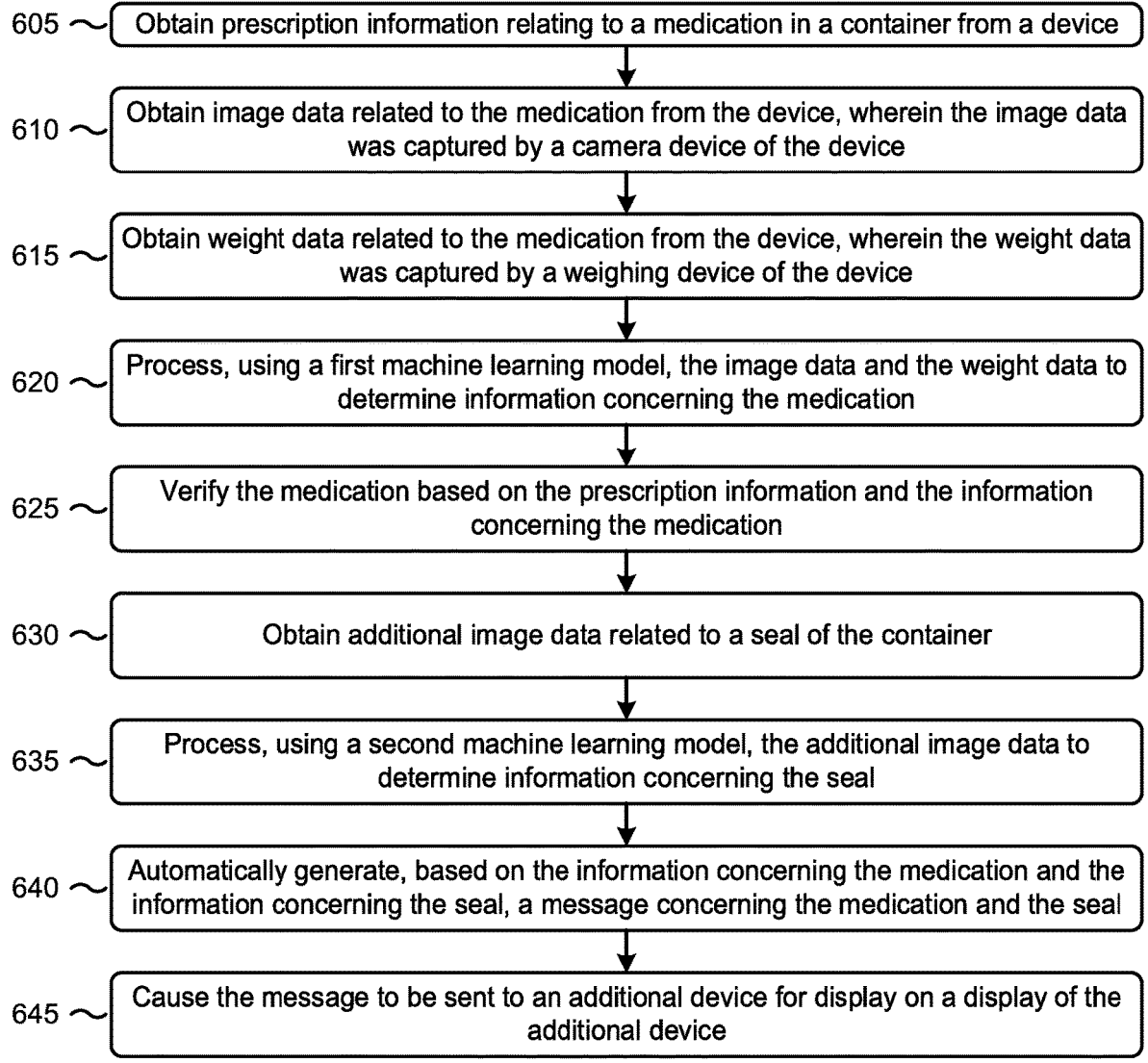

FIG. 6 is a flow chart of an example process 600 for identification and verification of medication. In some implementations, one or more process blocks of FIG. 6 may be performed by a medication identification and verification platform (e.g., medication identification and verification platform 330). In some implementations, one or more process blocks of FIG. 6 may be performed by another device or a group of devices separate from or including the medication identification and verification platform, such as a medication device (e.g., medication device 310) and/or the like.

As shown in FIG. 6, process 600 may include obtaining prescription information relating to a medication in a container from a device (block 605). For example, the medication identification and verification platform (e.g., using computing resource 334, processor 420, memory 430, storage component 440, input component 450, output component 460, communication interface 470 and/or the like) may obtain prescription information relating to a medication in a container from a device, as described above.

As further shown in FIG. 6, process 600 may include obtaining image data related to the medication from the device, wherein the image data was captured by a camera device of the device (block 610). For example, the medication identification and verification platform (e.g., using computing resource 334, processor 420, memory 430, storage component 440, input component 450, output component 460, communication interface 470 and/or the like) may obtain image data related to the medication from the device, as described above. In some implementations, the image data was captured by a camera device of the device.

As further shown in FIG. 6, process 600 may include obtaining weight data related to the medication from the device, wherein the weight data was captured by a weighing device of the device (block 615). For example, the medication identification and verification platform (e.g., using computing resource 334, processor 420, memory 430, storage component 440, input component 450, output component 460, communication interface 470 and/or the like) may obtain weight data related to the medication from the device, as described above. In some implementations, the weight data was captured by a weighing device of the device.

As further shown in FIG. 6, process 600 may include processing, using a first machine learning model, the image data and the weight data to determine information concerning the medication (block 620). For example, the medication identification and verification platform (e.g., using computing resource 334, processor 420, memory 430, storage component 440, input component 450, output component 460, communication interface 470 and/or the like) may process, using a first machine learning model, the image data and the weight data to determine information concerning the medication, as described above.

As further shown in FIG. 6, process 600 may include verifying the medication based on the prescription information and the information concerning the medication (block 625). For example, the medication identification and verification platform (e.g., using computing resource 334, processor 420, memory 430, storage component 440, input component 450, output component 460, communication interface 470 and/or the like) may verify the medication based on the prescription information and the information concerning the medication, as described above.

As further shown in FIG. 6, process 600 may include obtaining additional image data related to a seal of the container (block 630). For example, the medication identification and verification platform (e.g., using computing resource 334, processor 420, memory 430, storage component 440, input component 450, output component 460, communication interface 470 and/or the like) may obtain, after verifying the medication, additional image data related to a seal of the container, as described above.

As further shown in FIG. 6, process 600 may include processing, using a second machine learning model, the additional image data to determine information concerning the seal (block 635). For example, the medication identification and verification platform (e.g., using computing resource 334, processor 420, memory 430, storage component 440, input component 450, output component 460, communication interface 470 and/or the like) may process, using a second machine learning model, the additional image data to determine information concerning the seal, as described above.

As further shown in FIG. 6, process 600 may include automatically generating, based on the information concerning the medication and the information concerning the seal, a message concerning the medication and the seal (block 640). For example, the medication identification and verification platform (e.g., using computing resource 334, processor 420, memory 430, storage component 440, input component 450, output component 460, communication interface 470 and/or the like) may automatically generate, based on the information concerning the medication and the information concerning the seal, a message concerning the medication and the seal, as described above.

As further shown in FIG. 6, process 600 may include causing the message to be sent to an additional device for display on a display of the additional device (block 645). For example, the medication identification and verification platform (e.g., using computing resource 334, processor 420, memory 430, storage component 440, input component 450, output component 460, communication interface 470 and/or the like) may cause the message to be sent to an additional device for display on a display of the additional device, as described above.

Process 600 may include additional implementations, such as any single implementation or any combination of implementations described below and/or in connection with one or more other processes described elsewhere herein.

In some implementations, the first machine learning model has been trained to identify a medication, a dose of medication, and an amount of medication and to determine an identification confidence level based on historical image data and historical weight data, and, when processing the image data and the weight data to determine the information concerning the medication, the medication identification and verification platform may process the image data and the weight data using the first machine learning model to identify the medication, a dose of the medication, and an amount of the medication and determine an identification confidence level.

In some implementations, the information concerning the medication includes an identification of the medication, a dose of the medication, and an amount of the medication and an identification confidence level, and, when verifying the medication based on the prescription information and the information concerning the medication, the medication identification and verification platform may determine that the identification of the medication, the dose, and the amount of the medication corresponds to the prescription information, and may determine that the identification confidence level satisfies a threshold.

In some implementations, the image data may include image data concerning one or more of a size, a shape, a color, a pattern, a shading, a texture, a labeling, or a luminance of at least one individual unit of the medication. In some implementations, the weight data may include weight data concerning one or more of the container, the medication, or the seal. In some implementations, the second machine learning model has been trained to determine integrity issues concerning seals based on historical image data related to seals, and, when processing the additional image data to determine the information concerning the seal, the medication identification and verification platform may process the additional image data using the second machine learning model to determine whether the seal has an integrity issue.

In some implementations, the medication identification and verification platform may cause, after verifying the medication, the first machine learning model to be updated based on one or more of the image data, the weight data, the prescription information, or the information concerning the medication. In some implementations, the prescription information is obtained from a block chain, and, the medication identification and verification platform may cause the information concerning the medication and the information concerning the seal to be added to the block chain.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7:
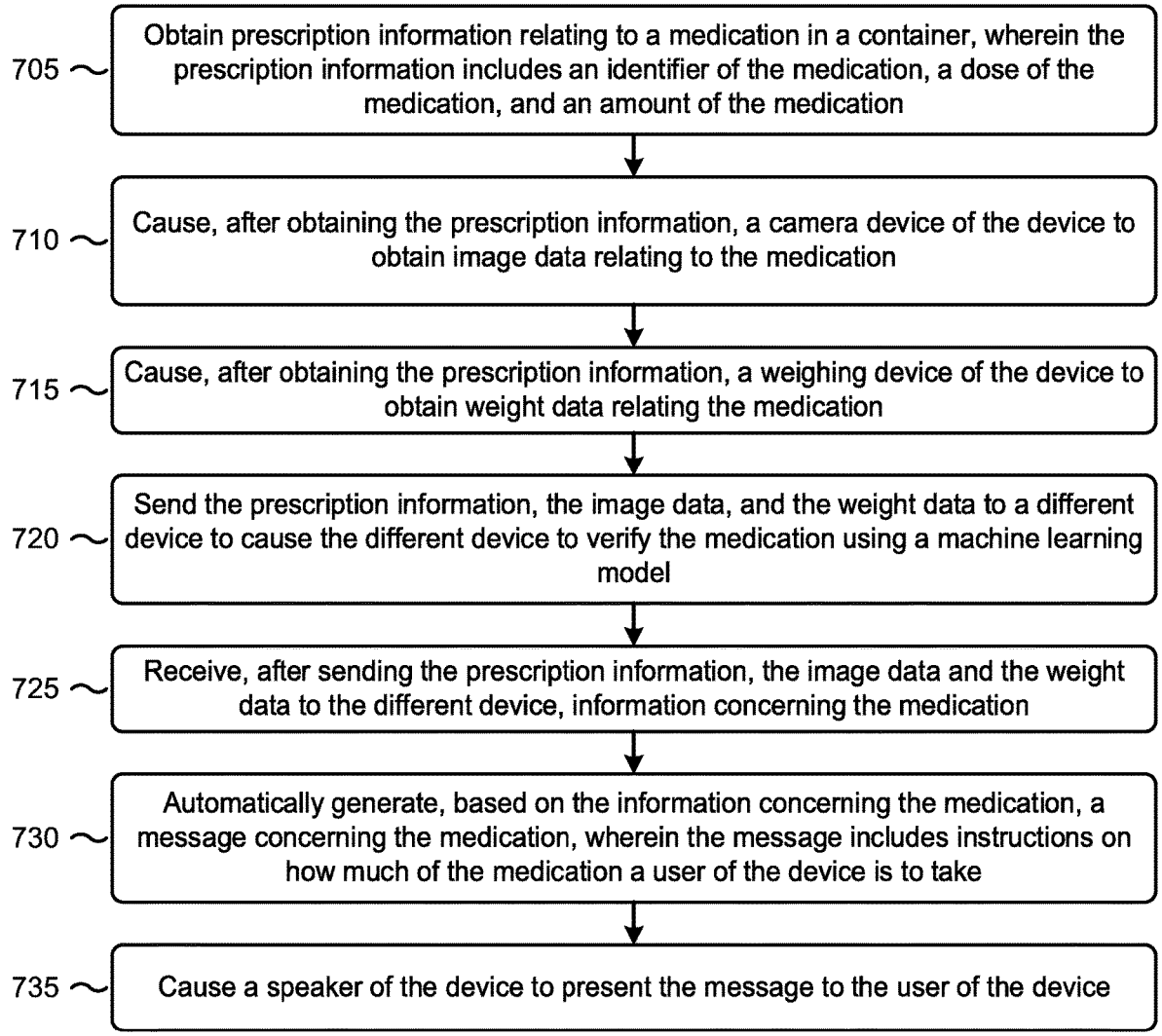

FIG. 7 is a flow chart of an example process 700 for identification and verification of medication. In some implementations, one or more process blocks of FIG. 7 may be performed by a medication device (e.g., medication device 310). In some implementations, one or more process blocks of FIG. 7 may be performed by another device or a group of devices separate from or including the medication device, such as a medication identification and verification platform (e.g., medication identification and verification platform 330) and/or the like.

As shown in FIG. 7, process 700 may include obtaining prescription information relating to a medication in a container, wherein the prescription information includes an identifier of the medication, a dose of the medication, and an amount of the medication (block 705). For example, the medication device (e.g., using processor 420, memory 430, storage component 440, input component 450, output component 460, communication interface 470 and/or the like) may obtain prescription information relating to a medication in a container, as described above. In some implementations, the prescription information includes an identifier of the medication, a dose of the medication, and an amount of the medication.

As further shown in FIG. 7, process 700 may include causing, after obtaining the prescription information, a camera device of the device to obtain image data relating to the medication (block 710). For example, the medication device (e.g., using processor 420, memory 430, storage component 440, input component 450, output component 460, communication interface 470 and/or the like) may cause, after obtaining the prescription information, a camera device of the device to obtain image data relating to the medication, as described above.

As further shown in FIG. 7, process 700 may include causing, after obtaining the prescription information, a weighing device of the device to obtain weight data relating the medication (block 715). For example, the medication device (e.g., using processor 420, memory 430, storage component 440, input component 450, output component 460, communication interface 470 and/or the like) may cause, after obtaining the prescription information, a weighing device of the device to obtain weight data relating the medication, as described above.

As further shown in FIG. 7, process 700 may include sending the prescription information, the image data, and the weight data to a different device to cause the different device to verify the medication using a machine learning model (block 720). For example, the medication device (e.g., using processor 420, memory 430, storage component 440, input component 450, output component 460, communication interface 470 and/or the like) may send prescription information, the image data, and the weight data to a different device to cause the different device to verify the medication using a machine learning model, as described above.

As further shown in FIG. 7, process 700 may include receiving, after sending the prescription information, the image data and the weight data to the different device, information concerning the medication (block 725). For example, the medication device (e.g., using processor 420, memory 430, storage component 440, input component 450, output component 460, communication interface 470 and/or the like) may receive, by the device and after sending the prescription information, the image, data and the weight data to the different device, information concerning the medication, as described above.

As further shown in FIG. 7, process 700 may include automatically generating, based on the information concerning the medication, a message concerning the medication, wherein the message includes instructions on how much of the medication a user of the device is to take (block 730). For example, the medication device (e.g., using processor 420, memory 430, storage component 440, input component 450, output component 460, communication interface 470 and/or the like) may automatically generate, based on the information concerning the medication, a message concerning the medication, as described above. In some implementations, the message includes instructions on how much of the medication a user of the device is to take.

As further shown in FIG. 7, process 700 may include causing a speaker of the device to present the message to the user of the device (block 735). For example, the medication device (e.g., using processor 420, memory 430, storage component 440, input component 450, output component 460, communication interface 470 and/or the like) may cause a speaker of the device to present the message to the user of the device, as described above.

Process 700 may include additional implementations, such as any single implementation or any combination of implementations described below and/or in connection with one or more other processes described elsewhere herein.

In some implementations, the medication device may cause, after causing the speaker to present the message, the camera device to obtain further image data relating to the medication; may cause, after causing the speaker to present the message, the weighing device to obtain further weight data concerning the medication; and may send the further image data and the further weight data to the different device to cause the different device to determine an amount of medication removed from the container using the machine learning model. In some implementations, the medication device may receive, after sending the further image data and the further weight data to the different device, additional information concerning the medication; may automatically generate, based on the additional information concerning the medication, an additional message concerning the medication; and may cause the speaker of the device to present the additional message to the user of the device. In some implementations, the additional message includes information on whether the amount of medication removed from the container is correct.

In some implementations, when causing the camera device to obtain the image data relating to the medication, the medication device may cause the camera device to determine when the container is in a field of view of the camera device; may cause the camera device to focus on the medication in the container; and may cause the camera device to capture the image data relating to the medication. In some implementations, when causing the speaker of the device to present the message to the user of the device, the medication device may generate, based on the message, voice data using a text-to-speech technique and may cause the speaker of the device to emit the voice data.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
   one or more memories; and one or more processors, communicatively coupled to the one or more memories, to:
- obtain prescription information relating to a medication in a container;
- cause, after obtaining the prescription information, a camera device of the device to obtain image data relating to the medication while the medication is in the container;
- cause, after obtaining the prescription information, a weighing device of the device to obtain weight data concerning the medication while the medication is in the container;
- send the image data and the weight data to a different device to cause the different device to identify the medication using a first machine learning model;
- receive, after sending the image data and the weight data, information concerning the medication from the different device;
- verify the medication based on the prescription information and the information concerning the medication;
- cause, after verifying the medication, the first machine learning model to be retrained using one or more of the image data, the weight data, the prescription information, or the information concerning the medication;
- cause, based on verifying the medication, the camera device to obtain additional image data relating to a seal of the container;
- send the additional image data to the different device to cause the different device to determine an integrity of the seal using a second machine learning model;
- receive, after sending the additional image data, information concerning the integrity of the seal from the different device;
- automatically generate, based on the information concerning the medication and the information concerning the integrity of the seal, a message concerning the medication and the seal; and
- cause an additional device to display the message on a display of the additional device.

2. The device of claim 1, wherein the prescription information includes at least one of:
- an identifier of the medication;
- information identifying a dose of the medication; or
- information identifying an amount of the medication.

3. The device of claim 1, wherein the image data is first image data;
the additional image data is second image data;
wherein the one or more processors are further to:
- cause the camera device to obtain third image data relating to a label of the container; and
wherein the one or more processors, when obtaining the prescription information, are to:
- process the third image data using an image processing technique to obtain the prescription information.

4. The device of claim 1, wherein the one or more processors are further to:
- cause ambient light to illuminate the container; and
wherein the one or more processors, when causing the camera device to obtain the image data relating to the medication, are to:
- cause the camera device to obtain the image data while the container is illuminated with the ambient light.

5. The device of claim 1, wherein the one or more processors are further to:
- determine that an identifier of the medication included in the prescription information matches an identifier of the medication included in the information concerning the medication;
- determine that a dose of the medication identified in the prescription information matches a dose of the medication identified in the information concerning the medication; and
- determine that an amount of the medication identified in the prescription information corresponds, within a threshold, to an amount of the medication identified in the information concerning the medication; and
wherein the one or more processors, when verifying the medication based on the prescription information and the information concerning the medication, are to:
- verify the medication based on determining that the identifier of the medication included in the prescription information matches the identifier of the medication included in the information concerning the medication, determining that the dose of the medication identified in the prescription information matches the dose of the medication identified in the information concerning the medication, and determining that the amount of the medication identified in the prescription information corresponds, within the threshold, to the amount of the medication identified in the information concerning the medication.

6. The device of claim 1, wherein the one or more processors are further to:
- determine that the container has been placed in a receptacle of the device; and
wherein the one or more processors, when causing the camera device to obtain the additional image data relating to the seal of the container, are to:
- cause the camera device to obtain the additional image data via a window of the receptacle.

7. The device of claim 1, wherein the one or more processors are further to:
- determine, based on the prescription information, an identifier of the additional device; and
wherein the one or more processors, when causing the additional device to display the message on the display of the additional device, are to:
- send, based on the identifier of the additional device, the message to the additional device.

8. The device of claim 1, wherein the one or more processors are further to:
- store the information concerning the medication and the information concerning the integrity of the seal in a blockchain,
  - wherein the blockchain is accessible by at least one device associated with manufacturing, filling, or distributing the medication.

9. A non-transitory computer-readable medium storing instructions, the instructions comprising:
one or more instructions that, when executed by one or more processors of a server device, cause the one or more processors to:
- obtain prescription information relating to a medication in a container from a device;
- obtain image data related to the medication from the device,
  - wherein the image data was captured by a camera device of the device;
- obtain weight data related to the medication from the device, wherein the weight data was captured by a weighing device of the device;
process, using a first machine learning model, the image data and the weight data to determine information concerning the medication;
verify the medication based on the prescription information and the information concerning the medication;
cause, after verifying the medication, the first machine learning model to be retrained using one or more of the image data, the weight data, the prescription information, or the information concerning the medication;
obtain additional image data related to a seal of the container;
process, using a second machine learning model, the additional image data to determine information concerning the seal;
automatically generate, based on the information concerning the medication and the information concerning the seal, a message concerning the medication and the seal; and
cause the message to be sent to an additional device for display on a display of the additional device.

10. The non-transitory computer-readable medium of claim 9, wherein the first machine learning model has been trained to identify a medication, a dose of medication, and an amount of medication and to determine an identification confidence level based on historical image data and historical weight data,
wherein the one or more instructions, that cause the one or more processors to process the image data and the weight data to determine the information concerning the medication, cause the one or more processors to:
process the image data and the weight data using the first machine learning model to identify the medication, the dose of the medication, and the amount of the medication and to determine the identification confidence level.

11. The non-transitory computer-readable medium of claim 9, wherein the information concerning the medication includes an identification of the medication, a dose of the medication, an amount of the medication, and an identification confidence level,
wherein the one or more instructions, that cause the one or more processors to verify the medication based on the prescription information and the information concerning the medication, cause the one or more processors to:
determine that the identification of the medication, the dose, and the amount of the medication corresponds to the prescription information; and
determine that the identification confidence level satisfies a threshold.

12. The non-transitory computer-readable medium of claim 9, wherein the image data includes image data concerning one or more of a size, a shape, a color, a pattern, a shading, a texture, a labeling, or a luminance of at least one individual unit of the medication.

13. The non-transitory computer-readable medium of claim 9, wherein the weight data includes weight data concerning one or more of the container, the medication, or the seal.

14. The non-transitory computer-readable medium of claim 9, wherein the second machine learning model has been trained to determine integrity issues concerning seals based on historical image data related to seals,
wherein the one or more instructions, that cause the one or more processors to process the additional image data to determine the information concerning the seal, cause the one or more processors to:
process the additional image data using the second machine learning model to determine whether the seal has an integrity issue.

15. The non-transitory computer-readable medium of claim 9, wherein the prescription information is obtained from a block chain,
wherein the one or more instructions, when executed by the one or more processors, further cause the one or more processors to:
cause the information concerning the medication and the information concerning the seal to be added to the block chain.

16. The non-transitory computer-readable medium of claim 9, wherein the message includes at least one of:
an indication that the medication has been verified,
an indication that an integrity of the seal has been verified,
a warning that the medication may be counterfeit, or
a warning that the integrity of the seal has been compromised.

17. A method, comprising:
obtaining, by a device, prescription information relating to a medication in a container;
causing, by the device and after obtaining the prescription information, a camera device of the device to obtain image data relating to the medication while the medication is in the container;
causing, by the device and after obtaining the prescription information, a weighing device of the device to obtain weight data concerning the medication while the medication is in the container;
sending, by the device, the image data and the weight data to a different device to cause the different device to identify the medication using a first machine learning model;
receiving, by the device and after sending the image data and the weight data, information concerning the medication from the different device;
verifying, by the device, the medication based on the prescription information and the information concerning the medication;
causing, by the device and after verifying the medication, the first machine learning model to be retrained using one or more of the image data, the weight data, the prescription information, or the information concerning the medication;
causing, by the device and based on verifying the medication, the camera device to obtain additional image data relating to a seal of the container;
sending, by the device, the additional image data to the different device to cause the different device to determine an integrity of the seal using a second machine learning model;
receiving, by the device and after sending the additional image data, information concerning the integrity of the seal from the different device;
automatically generating, by the device and based on the information concerning the medication and the information concerning the integrity of the seal, a message concerning the medication and the seal; and
causing, by the device, an additional device to display the message on a display of the additional device.

18. The method of claim 17, wherein the image data is first image data;

the additional image data is second image data;
wherein the method further comprises:
- causing the camera device to obtain third image data relating to a label of the container; and wherein obtaining the prescription information comprises:
- processing the third image data using an image processing technique to obtain the prescription information.

19. The method of claim 17, further comprising:
- determining that an identifier of the medication included in the prescription information matches an identifier of the medication included in the information concerning the medication;
- determining that a dose of the medication identified in the prescription information matches a dose of the medication identified in the information concerning the medication; and
- determining that an amount of the medication identified in the prescription information corresponds, within a threshold, to an amount of the medication identified in the information concerning the medication; and wherein verifying the medication based on the prescription information and the information concerning the medication comprises
- verifying the medication based on determining that the identifier of the medication included in the prescription information matches the identifier of the medication included in the information concerning the medication, determining that the dose of the medication identified in the prescription information matches the dose of the medication identified in the information concerning the medication, and determining that the amount of the medication identified in the prescription information corresponds, within the threshold, to the amount of the medication identified in the information concerning the medication.

20. The method of claim 17, further comprising:
- determining, based on the prescription information, an identifier of the additional device; and wherein causing the additional device to display the message on the display of the additional device comprises:
- sending, based on the identifier of the additional device, the message to the additional device.

* * * * *